(12) United States Patent
Watson et al.

(10) Patent No.: US 8,383,665 B2
(45) Date of Patent: Feb. 26, 2013

(54) IMMUNOMODULATORY COMPOSITIONS

(75) Inventors: Alison Ann Watson, Ceredigion (GB);
Robert James Nash, Ceredigion (GB);
Emma Louisa Evinson, Peterborough (GB)

(73) Assignee: Summit (Wales) Limited, Oxfordshire (GB)

( * ) Notice: Subject to any disclaimer, the term of this patent is extended or adjusted under 35 U.S.C. 154(b) by 183 days.

(21) Appl. No.: 10/543,014

(22) PCT Filed: Jan. 21, 2004

(86) PCT No.: PCT/GB2004/000198
§ 371 (c)(1),
(2), (4) Date: Aug. 15, 2006

(87) PCT Pub. No.: WO2004/064715
PCT Pub. Date: Aug. 5, 2004

(65) Prior Publication Data
US 2007/0155814 A1    Jul. 5, 2007

(30) Foreign Application Priority Data
Jan. 23, 2003    (GB) .................................. 0301554.2

(51) Int. Cl.
*A61K 31/407* (2006.01)
*C07D 487/04* (2006.01)
(52) U.S. Cl. ....................................... 514/412; 548/453
(58) Field of Classification Search .................. None
See application file for complete search history.

(56) References Cited

PUBLICATIONS

Nash et al., caplus an 1995:141541.*
Immune-Strategy, http://www.avac.org/lib/libGFBR2f.htm (1995).*
Asano et al., Tetrahedron: Asymmetry 11 (2000) 1-8.*
www-redorbit-com (http://www.redorbit.com/modules/news/tools.php?tool=print&id=460088), 2005.*
Collins, Expert Opinion Investig Drugs (2007), 16(11), p. 1743-1751.*
Hacks Chemical Dictionary, Fourth Edition, Julius Grant, 1972, p. 203.*
MITNews, 2011, http://web.mit.edu/newsoffice/2011/antiviral-0810.html.*
Virus, 2011, http://en.wikipedia.org/wiki/Virus.*
HIV, 2011, http://www.thewellproject.org/en_US/HIV_The_Basics/What_is_HIV.jsp.*
UK Patent office search report on UK patent application GB 0301554.2.
Bell, et al., "Synthesis of Casuarines [Pentahydroxylated Pyrrolizidines] by Sodium Hydrogen Telluride-Induced Cyclisations of Azidodimesylates" *Tetrahedron Letters*, 38, 5869-5872 (1997).
Wormald, et al., "Configurational and conformational analysis of highly oxygenated pyrrolizidines: definitive identification of some naturally occurring 7a-epi-alexines" *Tetrahedron: Asymmetry*, 9, 2549-2558 (1998).
Nash, et al., "Casuarine: A Very Highly Oxygenated Pyrrolizidine Alkaloid" *Tetrahedron Letters*, 35, 7849-7852 (1994).
Denmark, et al., "Synthesis of (+)-Casuarine" *Organic Letters*, 1, 1311-1314 (1999).
Denmark, et al., "Synthesis of (+)-Casuarine" *J. Org. Chem.*, 62, 2875-2886 (2000).
Wormald, et al., "Casuarine-6-a-D-Glucoside from Casuarina Equisetifolia and Eugenia Jambolana" *Carbohydrate Letters*, 2, 169-174 (1996).
Abstract of: Kato, et al., "Australine and related alkaloids: easy structural confirmation by 13C NMR spectral data and biological activities" *Tetrahedron: Asymmetry*, 14, 3250331 (2003).

* cited by examiner

*Primary Examiner* — Sun Jae Loewe
(74) *Attorney, Agent, or Firm* — Heslin Rothenberg Farley & Mesiti P.C.

(57) ABSTRACT

Isolated immunomodulatory (e.g. immunostimulatory) polyhydroxlated pyrrolizidine compounds having the formula

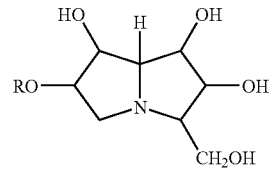

are disclosed. In these compounds R is selected from hydrogen, straight or branched, unsubstituted or substituted, saturated or unsaturated acyl, alkyl (e.g. cycloalkyl), alkenyl, alkynyl and aryl groups. The compounds are useful in therapy and prophylaxis, including increasing the Th1:Th2 response ratio, hemorestoration, alleviation of immunosuppression, cytokine stimulation, treatment of proliferative disorders (e.g. cancer), vaccination, stimulation of the innate immune response and boosting of the activity of endogenous NK cells.

14 Claims, 2 Drawing Sheets

IMMUNOMODULATORY COMPOSITIONS

CROSS REFERENCE TO RELATED APPLICATIONS

This application is a U.S. national phase filing under 35 U.S.C. 371 of PCT International Application PCT/GB2004/000198, filed Jan. 21, 2004, and published under PCT Article 21(2) in English as WO 2004/064715 on Aug. 5, 2004. PCT/GB2004/000198 claimed benefit from British Application 0301554.2, filed Jan. 23, 2003. The entire contents of each of the prior applications are incorporated herein by reference.

FIELD OF THE INVENTION

The present invention relates to immunomodulatory polyhydroxylated pyrrolizidine compounds and to their use in medicine. In particular, the invention relates to the use of casuarine and certain casuarine analogues as immunomodulatory (immunostimulatory or immunosuppressive) drugs.

BACKGROUND TO THE INVENTION

Immunity

When the immune system is challenged by a foreign antigen it responds by launching a protective response. This response is characterized by the coordinated interaction of both the innate and acquired immune systems. These systems, once thought to be separate and independent, are now recognized as two interdependent parts that when integrated fulfill two mutually exclusive requirements: speed (contributed by the innate system) and specificity (contributed by the adaptive system).

The innate immune system serves as the first line of defence against invading pathogens, holding the pathogen in check while the adaptive responses are matured. It is triggered within minutes of infection in an antigen-independent fashion, responding to broadly conserved patterns in the pathogens (though it is not non-specific, and can distinguish between self and pathogens). Crucially, it also generates the inflammatory and co-stimulatory milieu (sometimes referred to as the danger signal) that potentiates the adaptive immune system and steers (or polarizes it) towards the cellular or humoral responses most appropriate for combating the infectious agent (discussed in more detail below).

The adaptive response becomes effective over days or weeks, but ultimately provides the fine antigenic specificity required for complete elimination of the pathogen and the generation of immunologic memory. It is mediated principally by T and B cells that have undergone germline gene rearrangement and are characterized by an exquisite specificity and long-lasting memory. However, it also involves the recruitment of elements of the innate immune system, including professional phagocytes (macrophages, neutrophils etc.) and granulocytes (basophils, eosinophils etc.) that engulf bacteria and even relatively large protozoal parasites. Once an adaptive immune response has matured, subsequent exposure to the pathogen results in its rapid elimination (usually before symptoms of infection become manifest) because highly specific memory cells have been generated that are rapidly activated upon subsequent exposure to their cognate antigen.

Interdependence of Innate and Adaptive Responses

It is now thought that the earliest events following pathogen invasion are effected by cellular components of the innate immune system. The response is initiated when resident tissue macrophages and dendritic cells (DCs) encounter pathogen and become activated by signals generated by interaction between pattern-recognition receptors (PRRs) and the pathogen-associated molecular patterns (PAMPs) shared by large groups of microorganisms. The activated macrophages and DCs are stimulated to release various cytokines (including the chemokines IL-8, MIP-1$\alpha$ and MIP-1$\beta$), which constitute the danger signal and triggers an influx of Natural Killer (NK) cells, macrophages, immature dendritic cells into the tissues.

Loaded with antigen, the activated DCs then migrate to lymph nodes. Once there, they activate immune cells of the adaptive response (principally naïve B- and T-cells) by acting as antigen-presenting cells (APCs). The activated cells then migrate to the sites of infection (guided by the "danger signal") and once there further amplify the response by recruiting cells of the innate immune system (including eosinophils, basophils, monocytes, NK cells and granulocytes). This cellular trafficking is orchestrated by a large array of cytokines (particularly those of the chemokine subgroup) and involves immune cells of many different types and tissue sources (for a review, see Luster (2002), Current Opinion in Immunology 14: 129-135).

Polarization of the Adaptive Immune Response

The adaptive immune response is principally effected via two independent limbs: cell-mediated (type 1) immunity and antibody-mediated or humoral (type 2) immunity.

Type 1 immunity involves the activation of T-lymphocytes that either act upon infected cells bearing foreign antigens or stimulate other cells to act upon infected cells. This branch of the immune system therefore effectively contains and kills cells that are cancerous or infected with pathogens (particularly viruses). Type 2 immunity involves the generation of antibodies to foreign antigens by B-lymphocytes. This antibody-mediated branch of the immune system attacks and effectively neutralizes extracellular foreign antigens.

Both limbs of the immune system are important in fighting disease and there is an increasing realization that the type of immune response is just as important as its intensity or its duration. Moreover, since the type 1 and type 2 responses are not necessarily mutually exclusive (in many circumstances an effective immune response requires that both occur in parallel), the balance of the type 1/type 2 response (also referred to as the Th1:Th2 response ratio/balance by reference to the distinct cytokine and effector cell subsets involved in the regulation of each response—see below) may also play a role in determining the effectiveness (and repercussions) of the immune defence.

In many circumstances the immune response is skewed heavily towards a type 1 or type 2 response soon after exposure to antigen. The mechanism of this type 1/type 2 skewing or polarization is not yet fully understood, but is known to involve a complex system of cell-mediated chemical messengers (cytokines, and particularly chemokines) in which the type 1/type 2 polarization (or balance) is determined, at least in part, by the nature of the initial PRR-PAMP interaction when the DCs and macrophages of the innate immune system are first stimulated and subsequently by the cytokine milieu in which antigen priming of naïve helper T cells occurs.

Two cytokines in particular appear to have early roles in determining the path of the immune response. Interleukin-12 (IL-12), secreted by macrophages, drives the type 1 response by stimulating the differentiation of Th1 cells, the helper cells that oversee the type 1 response. Another macrophage cytokine, interleukin-10 (IL-10) inhibits this response, instead driving a type 2 response.

The type 1 and type 2 responses can be distinguished inter alia on the basis of certain phenotypic changes attendant on priming and subsequent polarization of naïve helper T cells.

These phenotypic changes are characterized, at least in part, by the nature of the cytokines secreted by the polarized helper T cells.

Th1 cells produce so-called Th1 cytokines, which include one or more of TNF, IL-1, IL-7, IFN-gamma, IL-12 and/or IL-18. The Th1 cytokines are involved in macrophage activation and Th1 cells orchestrate Type 1 responses. In contrast, Th2 cells produce so-called Th2 cytokines, which include one or more of IL-4, IL-5, IL-10 and IL-13. The Th2 cytokines promote the production of various antibodies and can suppress the type 1 response.

The involvement of Th1 and Th2 cells and cytokines in type 1:type 2 immune response polarization has given rise to the terms Th1 response and Th2 response being used to define the type 1 and type 2 immune responses, respectively. Thus, these terms are used interchangeably herein.

There is an increasing realization that the type of immune response is just as important in therapy and prophylaxis as its intensity or its duration. For example, an excess Th1 response can result in autoimmune disease, inappropriate inflammatory responses and transplant rejection. An excess Th2 response can lead to allergies and asthma. Moreover, a perturbation in the Th1:Th2 ratio is symptomatic of many immunological diseases and disorders, and the development of methods for altering the Th1:Th2 ratio is now a priority.

Alkaloids

The term alkaloid is used herein sensu stricto to define any basic, organic, nitrogenous compound which occurs naturally in an organism. The term alkaloid is also used herein sensu lato to define a broader grouping of compounds which include not only the naturally occurring alkaloids, but also their synthetic and semi-synthetic analogues and derivatives.

Most known alkaloids are phytochemicals, present as secondary metabolites in plant tissues (where they may play a role in defence), but some occur as secondary metabolites in the tissues of animals, microorganisms and fungi. There is growing evidence that the standard techniques for screening microbial cultures are inappropriate for detecting many classes of alkaloids (particularly highly polar alkaloids, see below) and that microbes (including bacteria and fungi, particularly the filamentous representatives) will prove to be an important source of alkaloids as screening techniques become more sophisticated.

Structurally, alkaloids exhibit great diversity. Many alkaloids are small molecules, with molecular weights below 250 Daltons. The skeletons may be derived from amino acids, though some are derived from other groups (such as steroids). Others can be considered as sugar analogues. It is becoming apparent (see Watson et al. (2001) Phytochemistry 56: 265-295) that the water soluble fractions of medicinal plants and microbial cultures contain many interesting novel polar alkaloids, including many carbohydrate analogues. Such analogues include a rapidly growing number of polyhydroxylated alkaloids.

Most alkaloids are classified structurally on the basis of the configuration of the N-heterocycle. Examples of some important alkaloids and their structures are set out in Kutchan (1995) The Plant Cell 7:1059-1070.

Watson et al. (2001) Phytochemistry 56: 265-295 have classified a comprehensive range of polyhydroxylated alkaloids inter alia as piperidine, pyrroline, pyrrolidine, pyrrolizidine, indolizidine and nortropanes alkaloids (see FIGS. 1-7 of Watson et al. (2001), the disclosure of which is incorporated herein by reference).

Watson et al. (2001), ibidem also show that a functional classification of at least some alkaloids is possible on the basis of their glycosidase inhibitory profile: many polyhydroxylated alkaloids are potent and highly selective glycosidase inhibitors. These alkaloids can mimic the number, position and configuration of hydroxyl groups present in pyranosyl or furanosyl moieties and so bind to the active site of a cognate glycosidase, thereby inhibiting it. This area is reviewed in Legler (1990) Adv. Carbohydr. Chem. Biochem. 48: 319-384 and in Asano et al., (1995) J. Med. Chem. 38: 2349-2356.

It has long been recognized that many alkaloids are pharmacologically active, and humans have been using alkaloids (typically in the form of plant extracts) as poisons, narcotics, stimulants and medicines for thousands of years. The therapeutic applications of polyhydroxylated alkaloids have been comprehensively reviewed in Watson et al. (2001), ibidem: applications include cancer therapy, immune stimulation, the treatment of diabetes, the treatment of infections (especially viral infections), therapy of glycosphingolipid lysosomal storage diseases and the treatment of autoimmune disorders (such as arthritis and sclerosis).

Both natural and synthetic mono- and bi-cyclic nitrogen analogues of carbohydrates are known to have potential as chemotherapeutic agents. Alexine (1) and australine (2) were the first pyrrolizidine alkaloids to be isolated with a carbon substituent at C-3, rather than the more common C-1 substituents characteristic of the necine family of pyrrolizidines.

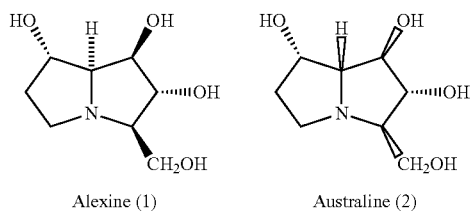 [SMILES: OC[C@@H]1[C@@H](O)[C@H](O)[C@@H]2[C@@H](O)CCN21 ; OC[C@@H]1[C@@H](O)[C@H](O)[C@H]2[C@@H](O)CCN21]

Alexine (1)  Australine (2)

The alexines occur in all species of the genus *Alexa* and also in the related species *Castanospermum australe*. Stereoisomers of alexine, including 1,7a-diepialexine (3), have also been isolated (Nash et al. (1990) Phytochemistry (29) 111) and synthesised (Choi et al. (1991) Tetrahedron Letters (32) 5517 and Denmark and Cottell (2001) J. Org. Chem. (66) 4276-4284).

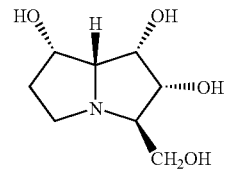

1,7a-diepialexine (3)

Because of the reported weak in vitro antiviral properties of one 7,7a-diepialexine (subsequently defined as 1,7a-diepialexine), there has been some interest in the isolation of the natural products and the synthesis of analogues.

As an indolizidine alkaloid (and so structurally distinct from the pyrrolizidine alexines), swainsonine (4) is a potent and specific inhibitor of α-mannosidase and is reported to have potential as an antimetastic, tumour anti-proliferative and immunoregulatory agent (see e.g. U.S. Pat. No. 5,650,413, WO00/37465, WO93/09117).

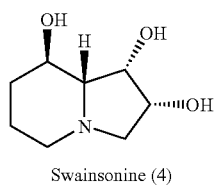

Swainsonine (4)

The effect of variation in the size of the six-membered ring of swainsonine on its glycosidase inhibitory activity has been studied: pyrrolizidine derivatives (so-called "ring contracted swainsonines") have been synthesised. However, these synthetic derivatives (1S,2R,7R,7aR)1,2,7-trihydroxypyrrolizidine (5) and the 7S-epimer (6)) were shown to have much weaker inhibitory activity relative to swainsonine itself (see U.S. Pat. No. 5,075,457).

(5)

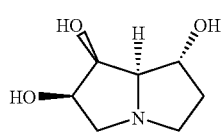

1S, 2R, 7R, 7aR)-1,2,7-trihydroxypyrrolizidine (6)

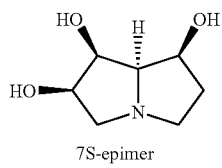

7S-epimer

Another compound, 1α,2α,6α,7α,7aβ-1,2,6,7-tetrahydroxypyrrolizidine (7) is an analogue of 1,8-diepiswainsonine and described as a "useful" inhibitor of glycosidase enzymes in EP0417059.

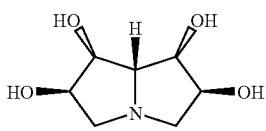

1α,2α,6α,7α,7aβ-1,2,6,7-tetrahydroxypyrrolizidine (7)

Casuarine, (1R,2R,3R,6S,7S,7aR)-3-(hydroxymethyl)-1,2,6,7-tetrahydroxypyrrolizidine (8) is a highly oxygenated bicyclic pyrrolizidine alkaloid that can be regarded as a more highly oxygenated analogue of the 1,7a-diepialexine (shown in 3) or as a C(3) hydroxymethyl-substituted analogue of the 1α,2α,6α,7α,7aβ-1,2,6,7-tetrahydroxypyrrolizidine (shown in 7).

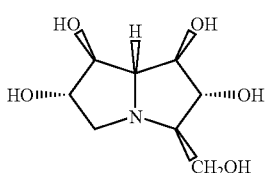

Casuarine (8)

Casuarine can be isolated from several botanical sources, including the bark of *Casuarina equisetifolia* (Casuarinaceae), the leaves and bark of *Eugenia janibolana* (Myrtaceae) and *Syzygium guineense* (Myrtaceae) (see e.g. Nash et al. (1994) Tetrahedron Letters (35) 7849-7852). Epimers of casuarine, and probably casuarine itself, can be synthesised by sodium hydrogen telluride-induced cyclisation of azidodimesylates (Bell et al. (1997) Tetrahedron Letters (38) 5869-5872).

*Casuarina equisetifolia* wood, bark and leaves have been claimed to be useful against diarrhoea, dysentery and colic (Chopra et al. (1956) Glossary of Indian Medicinal Plants, Council of Scientific and Industrial Research (India), New Delhi, p. 55) and a sample of bark has recently been prescribed in Western Samoa for the treatment of breast cancer. An African plant containing casuarine (identified as *Syzygium guineense*) has been reported to be beneficial in the treatment of AIDS patients (see Wormald et al. (1996) Carbohydrate Letters (2) 169-174).

The casuarine-6-α-glucoside (casuarine-6-α-D-glucopyranose, 9) has also been isolated from the bark and leaves of *Eugenia jambolana* (Wormald et al. (1996) Carbohydrate Letters (2) 169-174).

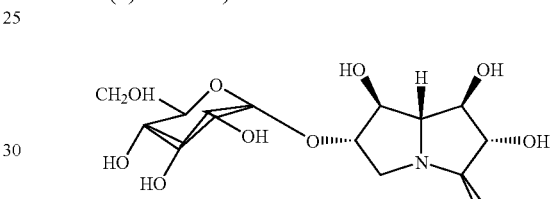

Casuarine-6-α-D-glucopyranose (9)

*Eugenia jambolana* is a well known tree in India for the therapeutic value of its seeds, leaves and fruit against diabetes and bacterial infections. Its fruit have been shown to reduce blood sugar levels in humans and aqueous extracts of the bark are claimed to affect glycogenolysis and glycogen storage in animals (Wormald et al. (1996) Carbohydrate Letters (2) 169-174).

Dendritic Cells and their Immunotherapeutic Uses (a) Introduction

Dendritic cells (DCs) are a heterogeneous cell population with distinctive morphology and a widespread tissue distribution (see Steinman (1991) Ann. Rev. Immunol. 9: 271-296). They play an important role in antigen presentation, capturing and processing antigens into peptides and then presenting them (together with components of the MHC) to T cells. T cell activation may then be mediated by the expression of important cell surface molecules, such as high levels of MHC class I and II molecules, adhesion molecules, and costimulatory molecules.

Dendritic cells therefore act as highly specialized antigen-presenting cells (APCs): serving as "nature's adjuvants", they potentiate adaptive T-cell dependent immunity as well as triggering the natural killer (NK and NKT) cells of the innate immune system. Dendritic cells therefore play a fundamental and important regulatory role in the magnitude, quality, and memory of the immune response. As a result, there is now a growing interest in the use of dendritic cells in various immunomodulatory interventions, which are described in more detail below.

Dendritic cells can be classified into different subsets inter alia on the basis of their state of maturation (mature or immature) and their cellular developmental origin (ontogeny). Each of these subsets appear to play distinct roles in vivo, as described below.

(b) Dendritic Cell Maturation

Immature (or resting) DCs are located in non-lymphoid tissue, such as the skin and mucosae, are highly phagocytic and readily internalize soluble and particulate antigens. It is only when such antigen-loaded immature DCs are also subject to inflammatory stimuli (referred to as maturation stimuli) that they undergo a maturation process that transforms them from phagocytic and migratory cells into non-phagocytic, highly efficient stimulators of naïve T cells.

Immature DCs are characterized by high intracellular MHC II in the form of MIICs, the expression of CD1a, active endocytosis for certain particulates and proteins, presence of FcgR and active phagocytosis, deficient T cell sensitization in vitro, low/absent adhesive and costimulatory molecules (CD40/54/58/80/86), low/absent CD25, CD83, p55, DEC-205, 2A1antigen, responsiveness to GM-CSF, but not M-CSF and G-CSF and a sensitivity to IL-10, which inhibits maturation.

Upon maturation, mature DCs, loaded with antigen and capable of priming T cells, migrate from the non-lymphoid tissues to the lymph nodes or spleen, where they process the antigen load and present it to the resident naïve $CD4^+$ T cells and $CD8^+$ cytotoxic T cells. This latter interaction generates CTLs, the cellular arm of the adaptive immune response, and these cells eliminate virally infected cells and tumour cells. The naïve $CD4^+$ T cells differentiate into memory helper T cells, which support the differentiation and expansion of $CD8^+$ CTLs and B cells. Thus, helper T cells exert antitumour activity indirectly through the activation of important effector cells such as macrophages and CTLs.

Having activated the T cells in this way, the mature DCs undergo apoptosis within 9-10 days.

Mature DC cells are characterized morphologically by motility and the presence of numerous processes (veils or dendrites). They are competent for antigen capture and presentation (exhibiting high MHC class I and II expression) and express a wide range of molecules involved in T cell binding and costimulation, (e.g. CD40, CD54/ICAM-1, CD58/LFA-3, CD80/B7-1 and CD86/B7-2) as well as various cytokines (including IL-12). They are phenotypically stable: there is no reversion/conversion to macrophages or lymphocytes.

Thus, mature DCs play an important role in T cell activation and cell-mediated immunity. In contrast, immature DCs are involved in regulating and maintaining immunological tolerance (inducing antigen-specific T cell energy).

(c) Dendritic Cell Ontogenic Subsets

Dendritic cells are not represented by a single cell type, but rather comprise a heterogeneous collection of different classes of cells, each with a distinct ontogeny. At least three different developmental pathways have been described, each emerging from unique progenitors and driven by particular cytokine combinations to DC subsets with distinct and specialized functions.

At present it is thought that the earliest DC progenitors/precursors common to all DCs originate in the bone marrow. These primitive progenitors are $CD34^+$, and they are released from the bone marrow to circulate through both the blood and lymphoid organs.

Once released from the bone marrow, the primitive $CD34^+$ DC progenitors are subject to various stimulatory signals. These signals can direct the progenitors along one of at least three different pathways, each differing with respect to intermediate stages, cytokine requirements, surface marker expression and biological function.

Lymphoid DCs are a distinct subset of DCs that are closely linked to the lymphocyte lineage. This lineage is characterized by the lack of the surface antigens CD11b, CD13, CD14 and CD33. Lymphoid DCs share ancestry with T and natural killer (NK) cells, the progenitors for all being located in the thymus and in the T cell areas of secondary lymphoid tissues. The differentiation of lymphoid DCs is driven by Interleukins 2, 3 and 15 (IL-3, IL-2 and IL-1), but not by granulocyte macrophage colony-stimulating factor (GM-CSF). Functionally, lymphoid promote negative selection in the thymus (possibly by inducing fas-mediated apoptosis) and are costimulatory for $CD4^+$ and $CD8^+$ T cells. More recently, lymphoid-like DCs derived from human progenitors have also been shown to preferentially activate the Th2 response. Because of their capacity to induce apoptosis and their role in eliminating potentially self-reactive T cells, it has been suggested that lymphoid DCs primarily mediate regulatory rather than stimulatory immune effector functions.

Myeloid DCs are distinguished by a development stage in which there is expression of certain features associated with phagocytes. There appear to be at least two structurally and functionally distinct subsets. The first is defined antigenically as $CD14^-$, $CD34^+$, $CD68^-$ and $CD1a^+$ and sometimes referred to as DCs of the Langerhans cell type. This subset appears to prime T cells to preferentially activate Th1 responses and IL-12 appears implicated in this process. The subset may also activate naïve B cells to secrete IgM and may therefore be predominantly associated with an inflammatory Th1 response. A second myeloid DC subset, sometimes referred to as interstitial DCs, is defined antigenically as $CD14^+$, $CD68^+$ and $CD1a^-$ and related to monocytes (as a result they are also referred to as monocyte-derived DCs or Mo-DCs).

(d) Dendritic Cell Vaccines

In one dendritic cell-based treatment paradigm (reviewed in Schuler et al. (2003) Current Opinion in Immunol 15: 138-147), DC cells are taken from a patient (for example by apheresis) and then pulsed (primed or spiked) with a particular antigen or antigens (for example, tumour antigen(s)). They are then re-administered as an autologous cellular vaccine to potentiate an appropriate immune response.

In this treatment paradigm, the responding T cells include helper cells, especially Th1 $CD4^+$ cells (which produce IFN-γ) and killer cells (especially $CD8^+$ cytolytic T lymphocytes). The DCs may also mediate responses by other classes of lymphocytes (B, NK, and NKT cells). They may also elicit T cell memory, a critical goal of vaccination.

At present, little is known about the identity of the DC subset(s) required for optimum effectiveness of DC vaccines, beyond the recognition that maturation is required and immature DCs are to be avoided (Dhodapkar and Steinman (2002) Blood 100: 174-177).

Hsu et al. (1996) Nat Med 2: 52-58 used rare DCs isolated ex vivo from blood. These DCs were highly heterogeneous with respect to their ontogenic subsets but matured spontaneously during the isolation procedure. However, the yields were very low.

The yield problem has been addressed by the development of techniques for expanding the DCs ex vivo, for example with Flt3 ligand (Fong et al. (2001) PNAS 98: 8809-8814), but this is of limited effectiveness.

However, most studies have used Mo-DCs. These cells are obtained by exposing monocytes to GM-CSF and IL-4 (or IL-13) to produce immature Mo-DCs, which are then matured by incubation in a maturation medium. Such media comprise one or more maturation stimulation factor(s), and typically comprise Toll-like receptor (TLR) ligands (e.g. microbial products such as lipopolysaccharide and/or monophosphoryl lipid), inflammatory cytokines (such as TNF-α), CD40L, monocyte conditioned medium (MCM) or MCM mimic (which contains IL-1β, TNF-α, IL-6 and $PGE_2$).

Although little is known at present about the influence of maturation medium on DC vaccine performance, MCM or MCM mimic currently represent a standard: Mo-DCs matured using these media are homogenous, have a high viability, migrate well to chemotactic stimuli and induce CTLs both in vitro and in vivo.

Techniques have been developed for generating large numbers of Mo-DCs (300 to 500 million mature DCs per apheresis) from adherent monocytes within semi-closed, multilayered communicating culture vessels offering a surface area large enough to cultivate one leuk-apheresis product. These so-called cell factories can be used to produce cryopreserved aliquots of antigen preloaded DCs which are highly viable on thawing, and optimised maturation and freezing procedures have been described (Berger et al. (2002) J. Immunol. Methods 268: 131-140; Tuyaerts et al. (2002) J. Immunol. Methods 264: 135-151).

Dendritic cells for vaccination have also been prepared from $CD34^+$-derived DCs comprising a mixture of interstitial and DCs of the Langerhans cell type. Some workers believe that the latter DC subset are more potent than Mo-DCs when used as DC vaccines.

With regard to antigen selection, various approaches have been used. Both defined and undefined antigens can be employed. The antigens can be xenoantigens or autoantigens. One or more defined neoantigen(s) may be selected: in the case of cancer treatment, the neoantigen(s) may comprise a tumour-associated antigen. However, most popular are 9-11 amino acid peptides containing defined antigens (either natural sequences or analogues designed for enhanced MHC binding): such antigens can be manufactured to good manufacturing practice (GMP) standard and are easily standardized.

Other approaches have employed antigens as immune complexes, which are delivered to Fc-receptor-bearing DCs and which results in the formation of both MHC class I and MHC class II peptide sequences. This offers the potential for inducing both CTLs and Th cells (Berlyn et al. (2001) Clin Immunol 101: 276-283).

Methods have also been developed for exploring the whole antigenic repertoire of any given tumour (or other target cell, such as a virally-infected cell). For example, DC-tumour cell hybrids have been successfully used to treat renal cell carcinoma (Kugler et al. (2000) 6: 332-336), but the hybrids are difficult to standardize and short-lived. Necrotic or apoptotic tumour cells have been used, as have various cellular lysates.

It appears that the selection of patient-specific antigens may be important in the treatment of at least some cancers, and antigens derived from fresh tumour cells rather than tumour cell lines or defined antigens may prove important (Dhodapkar et al. (2002) PNAS 99: 13009-13013).

As regards delivery of the selected antigen(s) to the DCs, various techniques are available. Since the number and quality of MHC-peptide complexes directly influences the immunogenicity of the DC, the antigen loading technique may prove critical to DC vaccine performance (van der Burg et al. (1996) J Immunol 156: 3308-3314). It seems that prolonged presentation of MHC-peptide complexes by the DCs enhances immunogenicity and so loading techniques which promote prolonged presentation may be important. This has been achieved by loading the DCs internally through the use of peptides linked to cell-penetrating moieties (Wang and Wang (2002) Nat Biotechnol 20: 149-154).

Antigens can also be loaded by transfecting the DCs with encoding nucleic acid (e.g. by electroporation) such that the antigens are expressed by the DC, processed and presented at the cell surface. This approach avoids the need for expensive GMP proteins and antibodies. RNA is preferred for this purpose, since it produces only transient expression (albeit sufficient for antigen processing) and avoids the potential problems associated with the integration of DNA and attendant long-term expression/mutagenesis. Such transfection techniques also permit exploration of the whole antigenic repertoire of a target cell by use of total or PCR-amplified tumour RNA.

There is some evidence that helper proteins (for example, keyhole limpet hemocyanin (KLH) and tetanus toxoid (TT)) can provide unspecific help for CTL induction (Lanzavecchia (1998) Nature 393: 413-414) and it may prove advantageous to pulse DC with such helper proteins prior to vaccination.

With regard to posology, the dose, frequency and route of DC vaccine administration have not yet been optimised in clinical trials. Clearly, the absolute number of cells administered will depend on the route of administration and effectiveness of migration after infusion. In this respect there are indications that intradermal or subcutaneous administration may be preferred for the development of Th1 responses, although direct intranodal delivery has been employed to circumvent the need for migration from the skin to the nodes (Nestle et al. (1998) Nat Med 4: 328-332).

Quite distinct from the antigen-pulsed DC vaccine paradigm described above is an approach in which dendritic cells secreting various chemokines are injected directly into tumours where they have been shown to prime T cells extranodally (Kirk et al. (2001) Cancer Res 61: 8794-8802). Thus, in another treatment paradigm, DCs are targeted to a tumour and activated to elicit immune responses in situ without the need for ex vivo antigen loading.

In situ DC vaccination constitutes yet another distinct (but related) approach (Hawiger et al. (2001) J Exp Med 194: 769-779. In this therapeutic paradigm, antigen is targeted to DCs in vivo which are expanded and induced to mature in situ. This approach depends on efficient targeting of antigen to endogenous DCs (for example, using exosomes—see Thery et al. (2002) Nat Rev Immunol 2: 569-579) and the development of maturation stimulants that can effectively trigger maturation (preferably of defined DC subset(s)) in vivo.

(e) Use of Dendritic Cells in Adoptive CTL Immunotherapy

Cytotoxic T lymphocytes (CTLs) can be administered to a patient in order to confer or supplement an immune response to a particular disease or infection (typically cancer). For example, tumour specific T cells can be extracted from a patient (e.g. by leukapheresis), selectively expanded (for example by tetramer-guided cloning—see Dunbar et al. (1999) J Immunol 162: 6959-6962) and then re-administered as an autologous cellular vaccine.

The clinical effectiveness, applicability and tractability of this type of passive immunotherapy can be greatly increased by using dendritic cells to prime the T cells in vitro prior to administration.

(f) Dendritic Cell-Based Approaches to the Treatment of Autoimmune Disorders

Dendritic cells are also involved in regulating and maintaining immunological tolerance: in the absence of maturation, the cells induce antigen-specific silencing or tolerance.

Thus, in another dendritic cell-based treatment paradigm, immature DCs are administered as part of an immunomodulatory intervention designed to combat autoimmune disorders. In such applications, the suppressive potential of the DCs has been enhanced by in vitro transfection with genes encoding cytokines.

(g) The Role of IL-2 in Dendritic Cell Function

Granucci et al. (2002) Trends in Immunol. 23: 169-171 have reported transient upregulation of mRNA transcripts for IL-2 in dendritic cells following microbial stimulus. In WO03012078 Granucci describes the important role played by DC-derived IL-2 in mediating not only T cell activation but also that of NK cells and goes on to suggest that DC-derived IL-2 is a key factor regulating and linking innate and adaptive immunity.

Moreover, systemic administration of IL-2 has recently been shown to enhance the therapeutic efficacy of a DC vaccine (Shimizu et al. (1999) PNAS 96: 2268-2273), while the presence of IL-2 was shown to be essential for specific peptide-mediated immunity mediated by dendritic cells in at least some DC vaccination regimes (Eggert et al. (2002) Eur J Immunol 32: 122-127). In their recent review, Schuler et al. (ibidem) conclude that " . . . it might be worthwhile to explore the combination of DC vaccination with IL-2 administration, as the T-cell responses induced by DC vaccination appear enhanced and therapeutically more effective.".

It will be clear from the foregoing discussion that dendritic cells are now proven as valuable tools in immunotherapy (particularly in the treatment of cancer), but that DC vaccination is still at a relatively early stage. Methods for preparing DCs are improving continuously and an increasing number of Phase I, II and III clinical trials are driving intense research and development in this area. However, there is still a need to improve efficacy at the level of DC biology.

The present inventors have now surprisingly discovered that casuarine and certain casuarine analogues have unexpected immunomodulatory activity, and that this activity may not be dependent on glycosidase inhibition.

SUMMARY OF THE INVENTION

According to the invention there is provided an isolated immunomodulatory (e.g. immunostimulatory) polyhydroxylated pyrrolizidine compound for use in therapy or prophylaxis having the formula:

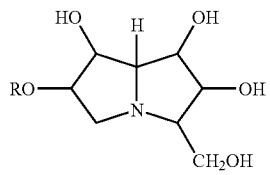

wherein R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof.

Preferably, the compounds of the invention are alkaloids (as hereinbefore defined).

The compound of the invention preferably has the formula:

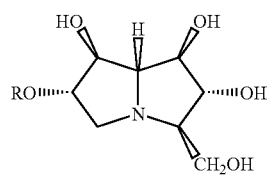

wherein R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof.

Particularly preferred is 1R,2R,3R,6S,7S,7aR)-3-(hydroxymethyl)-1,2,6,7-tetrahydroxypyrrolizidine (casuarine), wherein R is hydrogen and which has the formula:

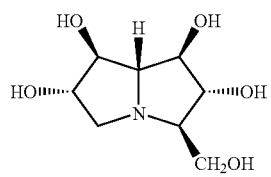

or a pharmaceutically acceptable derivative or salt thereof.

Particularly preferred is a casuarine glucoside, or a pharmaceutically acceptable salt or derivative thereof.

Other preferred compounds include 6-O-butanoylcasuarine of the formula:

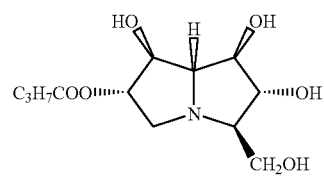

or a pharmaceutically acceptable salt or derivative thereof.

A particularly preferred casuarine glucoside is casuarine-6-α-D-glucoside of the formula:

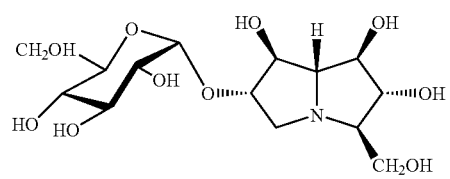

or a pharmaceutically acceptable salt or derivative thereof.

As mentioned infra, the invention contemplates diastereomers of the compounds of the invention. Particularly preferred are diastereomers selected from 3,7-diepisuarine (10), 7-epi-casuarine (11), 3,6,7-triepi-casuarine (12), 6,7-diepi-casuarine (13) and 3-epi-casuarine (14), as well as pharmaceutically acceptable salts and derivatives thereof.

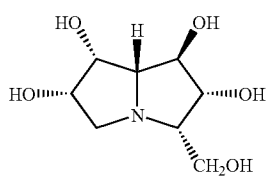 [SMILES: OC[C@H]1[C@@H](O)[C@H](O)[C@H]2[C@@H](O)[C@@H](O)CN21]
3,7-diepi-casuarine (10)

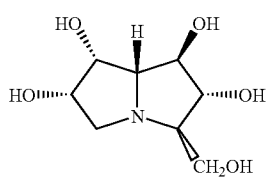
7-epicasuarine (11)

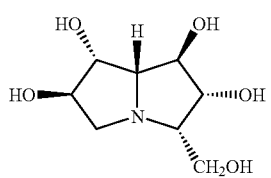
3,6,7-triepi-casuarine (12)

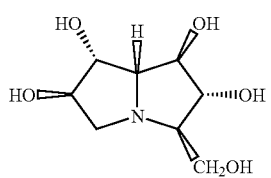
6,7-diepi-casuarine (13)

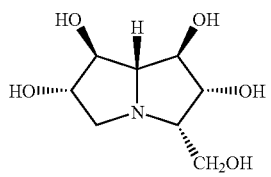 [SMILES: OC[C@H]1[C@@H](O)[C@H](O)[C@H]2[C@H](O)[C@@H](O)CN21]
3-epi-casuarine (14)

Other preferred diastereomers are selected from 3,7-diepi-casuarine-6-α-D-glucoside (15), 7-epi-casuarine-6-α-D-glucoside (16), 3,6,7-triepi-casuarine-6-α-D-glucoside (17), 6,7-diepi-casuarine-6-α-D-glucoside (18) and 3-epi-casuarine-6-α-D-glucoside (19), as well as pharmaceutically acceptable salts and derivatives thereof.

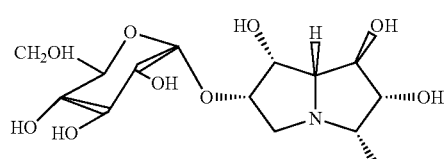
3,7-diepi-casuarine-6-α-D-glucoside (15)

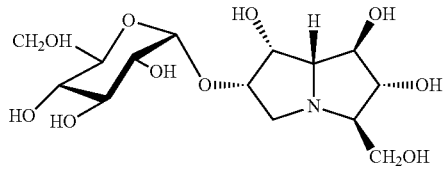
7-epi-casuarine-6-α-D-glucoside (16)

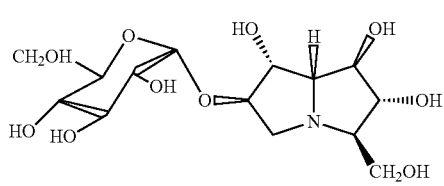
3,6,7-triepi-casuarine-6-α-D-glucoside (17)

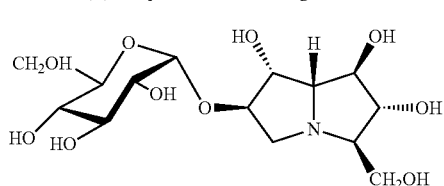
6,7-diepi-casuarine-6-α-D-glucoside (18)

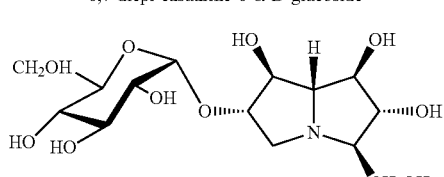
3-epi-casuarine-6-α-D-glucoside (19)

Other preferred diastereomers include 7a epimers selected from 3,7,7a-triepi-casuarine, 7,7a-diepi-casuarine, 3,6,7,7a-tetraepi-casuarine, 6,7,7a-triepi-casuarine and 3,7a-diepi-casuarine, as well as pharmaceutically acceptable salts and derivatives thereof.

In another aspect the invention provides a method for immunomodulation (e.g. immunostimulation) comprising administering to a patient a composition comprising a polyhydroxylated pyrrolizidine compound having the formula:

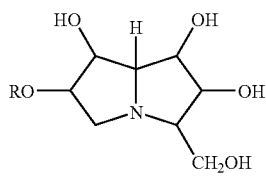

wherein R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof.

The immunostimulatory methods of the invention are described in more detail infra.

In another aspect, the invention provides a method for chemoprotection comprising administering the compound of the invention to a patient undergoing chemotherapy.

The invention also contemplates the use of the polyhydroxylated pyrrolizidine compound of the invention for the manufacture of a medicament for use in immunostimulation and/or chemoprotection, as well as a process for the manufacture of a medicament for use in immunostimulation and/or chemoprotection, characterized in the use of the polyhydroxylated pyrrolizidine compound of the invention.

In another aspect, the invention contemplates a composition comprising the polyhydroxylated pyrrolizidine compound of the invention in combination with an immunostimulant and/or cytotoxic agent (e.g. AZT) and/or an antimicrobial (e.g. antibacterial) agent and/or an antiviral agent and/or a dendritic cell (e.g. a primed dendritic cell). Such compositions preferably further comprise a pharmaceutically acceptable excipient.

In another aspect the invention contemplates a vaccine comprising the polyhydroxylated pyrrolizidine compound of the invention in combination with an antigen, the compound being present in an amount sufficient to produce an adjuvant effect on vaccination.

In another aspect the invention contemplates a pharmaceutical kit of parts comprising the polyhydroxylated pyrrolizidine compound of the invention in combination with an immunostimulant and/or cytotoxic agent (e.g. 5' fluoro-uracil and ricin) and/or an antimicrobial (e.g. antibacterial) agent and/or an antiviral agent (e.g. AZT). Such kits preferably further comprise instructions for use in immunotherapy.

The compounds of the invention have broad utility in therapy and prophylaxis, including treatments for increasing the Th1:Th2 response ratio, for example in the treatment of Th1-related diseases or disorders (e.g. proliferative disorders or microbial infection) and/or Th2-related diseases or disorders (for example allergies, e.g. asthma), as well as in haemorestoration, the alleviation of immunosuppression, in cytokine stimulation, in the treatment of proliferative disorders, vaccination (wherein the compound acts as an adjuvant), vaccination with dendritic cell vaccines (e.g. with primed dendritic cell vaccines, wherein the dendritic cells are contacted with the compound), in the administration of dendritc cells in the treatment or prophylaxis of autoimmune disorders (wherein the dendritic cells are contacted with the compound) and in wound healing. These medical uses are described in more detail below.

DETAILED DESCRIPTION OF THE INVENTION

Definitions

Figure 1:
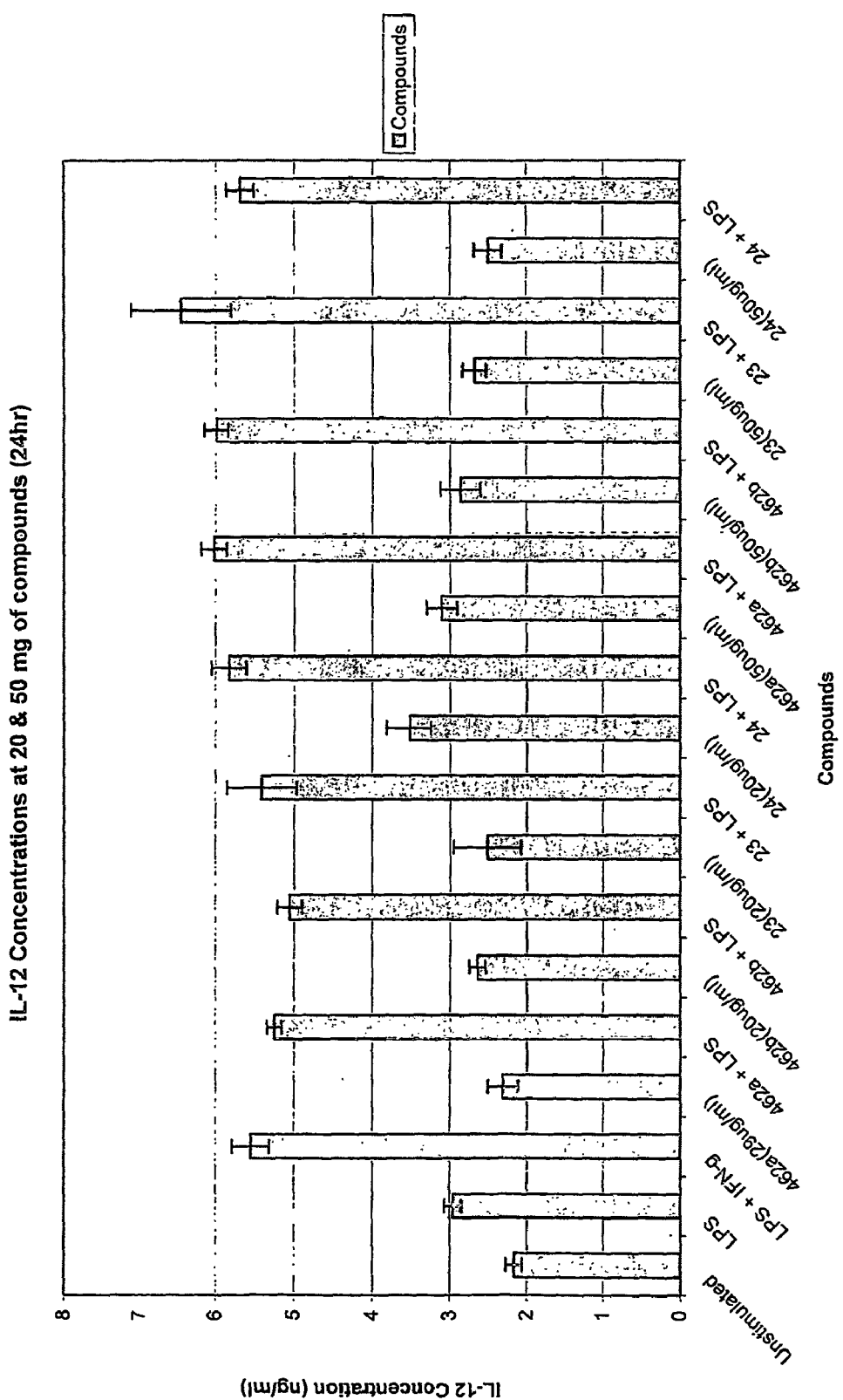
FIG. 1 shows IL-12 concentrations after treatment with some embodiments of the invention at 24 hours in an enzyme linked immunosorbent assay (ELISA).

Where used herein and unless specifically indicated otherwise, the following terms are intended to have the following meanings in addition to any broader (or narrower) meanings the terms might enjoy in the art:

The term adjunctive (as applied to the use of the drugs of the invention in therapy) defines uses in which the pyrrolizidine compound is administered together with one or more other drugs, interventions, regimens or treatments (such as surgery and/or irradiation). Such adjunctive therapies may comprise the concurrent, separate or sequential administration/application of the pyrrolizidine compound of the invention and the other treatment(s). Thus, in some embodiments, adjunctive use of the pyrrolizidine compound of the invention is reflected in the formulation of the pharmaceutical compositions of the invention. For example, adjunctive use may be reflected in a specific unit dosage, or in formulations in which the pyrrolizidine compound of the invention is present in admixture with the other drug(s) with which it is to be used adjunctively (or else physically associated with the other drug(s) within a single unit dose). In other embodiments, adjunctive use of the pyrrolizidine compound of the invention may be reflected in the composition of the pharmaceutical kits of the invention, wherein the pyrrolizidine compound of the invention is co-packaged (e.g. as part of an array or unit doses) with the other drug(s) with which it is to be used adjunctively. In yet other embodiments, adjunctive use of the pyrrolizidine compound of the invention may be reflected in the content of the information and/or instructions co-packaged with the pyrrolizidine compound relating to formulation and/or posology.

The term neoantigen is used herein to define any newly expressed antigenic determinant. Neoantigens may arise upon conformational change in a protein, as newly expressed determinants (especially on the surfaces of transformed or infected cells), as the result of complex formation of one or more molecules or as the result of cleavage of a molecule with a resultant display of new antigenic determinants. Thus, as used herein, the term neoantigen covers antigens expressed upon infection (e.g. viral infection, protozoal infection or bacterial infection), in prion-mediated diseases (e.g. BSE and CJD), an on cell transformation (cancer), in which latter case the neoantigen may be termed a tumour-associated antigen.

The term tumour-associated antigen is used herein to define an antigen present in transformed (malignant or tumourous) cells which is absent (or present in lower amounts or in a different cellular compartment) in normal cells of the type from which the tumour originated. Oncogenic viruses can also induce expression of tumour antigens, which are often host proteins induced by the virus.

The term herbal medicine is used herein to define a pharmaceutical composition in which at least one active principle is not chemically synthesized and is a phytochemical constituent of a plant. In most cases, this non-synthetic active principle is not isolated (as defined herein), but present together with other phytochemicals with which it is associated in the source plant. In some cases, however, the plant-derived bioactive principle(s) may be in a concentrated fraction or isolated (sometimes involving high degrees of purification). In many cases, however, the herbal medicine comprises a more or less crude extract, infusion or fraction of a plant or even an unprocessed whole plant (or part thereof, though in such cases the plant (or plant part) is usually at least dried and/or milled.

The term bioactive principle is used herein to define a phytochemical which is necessary or sufficient for the pharmaceutical efficacy of the herbal medicament in which it is comprised. In the case of the present invention, the bioactive principle comprises the immunomodulatory compound of the invention (e.g. casuarine, casuarine glucoside or mixtures thereof.

The term standard specification is used herein to define a characteristic, or a phytochemical profile, which is correlated with an acceptable quality of the herbal medicine. In this context, the term quality is used to define the overall fitness of the herbal medicament for its intended use, and includes the presence of one or more of the bioactive principles (at an appropriate concentration) described above or else the presence of one or more bioactive markers or a phytochemical profile which correlates with the presence of one or more of the bioactive principles (at an appropriate concentration).

The term phytochemical profile is used herein to define a set of characteristics relating to different phytochemical constituents.

The term isolated as applied to the pyrrolizidine compounds of the invention is used herein to indicate that the compound exists in a physical milieu distinct from that in which it occurs in nature. For example, the isolated material may be substantially isolated (for example purified) with respect to the complex cellular milieu in which it naturally occurs. When the isolated material is purified, the absolute level of purity is not critical and those skilled in the art can readily determine appropriate levels of purity according to the use to which the material is to be put. Preferred, however, are purity levels of 90% w/w, 99% w/w or higher. In some circumstances, the isolated compound forms part of a composition (for example a more or less crude extract containing many other substances) or buffer system, which may for example contain other components. In other circumstances, the isolated compound may be purified to essential homogeneity, for example as determined spectrophotometrically, by NMR or by chromatography (for example GC-MS).

The term pharmaceutically acceptable derivative as applied to the pyrrolizidine compounds of the invention define compounds which are obtained (or obtainable) by chemical derivatization of the parent pyrrolizidine compounds of the invention. The pharmaceutically acceptable derivatives are therefore suitable for administration to or use in contact with the tissues of humans without undue toxicity, irritation or allergic response (i.e. commensurate with a reasonable benefit/risk ratio). Preferred derivatives are those obtained (or obtainable) by alkylation, esterification or acylation of the parent pyrrolizidine compounds of the invention. The derivatives may be immunomodulatory per se, or may be inactive until processed in vivo. In the latter case, the derivatives of the invention act as pro-drugs. Particularly preferred pro-drugs are ester derivatives which are esterified at one or more of the free hydroxyls and which are activated by hydrolysis in vivo. The pharmaceutically acceptable derivatives of the invention retain some or all of the immunomodulatory activity of the parent compound. In some cases, the immunomodulatory activity is increased by derivatization. Derivatization may also augment other biological activities of the compound, for example bioavailability and/or glycosidase inhibitory activity and/or glycosidase inhibitory profile. For example, derivatization may increase glycosidase inhibitory potency and/or specificity.

The term pharmaceutically acceptable salt as applied to the pyrrolizidine compounds of the invention defines any non-toxic organic or inorganic acid addition salt of the free base compounds which are suitable for use in contact with the tissues of humans and lower animals without undue toxicity, irritation, allergic response and which are commensurate with a reasonable benefit/risk ratio. Suitable pharmaceutically acceptable salts are well known in the art. Examples are the salts with inorganic acids (for example hydrochloric, hydrobromic, sulphuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid). The drugs of the invention may also be converted into salts by reaction with an alkali metal halide, for example sodium chloride, sodium iodide or lithium iodide. Preferably, the pyrrolizidine compounds of the invention are converted into their salts by reaction with a stoichiometric amount of sodium chloride in the presence of a solvent such as acetone.

These salts and the free base compounds can exist in either a hydrated or a substantially anhydrous form. Crystalline forms of the compounds of the invention are also contemplated and in general the acid addition salts of the pyrrolizidine compounds of the invention are crystalline materials which are soluble in water and various hydrophilic organic solvents and which in comparison to their free base forms, demonstrate higher melting points and an increased solubility.

In its broadest aspect, the present invention contemplates all optical isomers, racemic forms and diastereomers of the pyrrolizidine compounds of the invention. Those skilled in the art will appreciate that, owing to the asymmetrically substituted carbon atoms present in the compounds of the invention, the pyrrolizidine compounds of the invention may exist and be synthesised and/or isolated in optically active and racemic forms. Thus, references to the pyrrolizidine compounds of the present invention encompass the pyrrolizidine compounds as a mixture of diastereomers, as individual diastereomers, as a mixture of enantiomers as well as in the form of individual enantiomers.

Therefore, the present invention contemplates all optical isomers and racemic forms thereof of the compounds of the invention, and unless indicated otherwise (e.g. by use of dash-wedge structural formulae) the compounds shown herein are intended to encompass all possible optical isomers of the compounds so depicted. In cases where the stereochemical form of the compound is important for pharmaceutical utility, the invention contemplates use of an isolated eutomer.

Biological Activities of the Compounds of the Invention

Without wishing to be bound by any theory, it is thought that the immunomodulatory activity of the compounds of the invention may arise from the stimulation and/or suppression of cytokine secretion in vivo. In particular, it is thought that that the immunomodulatory activity of the compounds of the invention arises from the stimulation of secretion of one or more cytokines (e.g. one or more Th1 cytokines), including interleukins 2 and/or 12 (IL-2 and/or IL-12) and/or the suppression of secretion of one or more Th2 cytokines (e.g. IL-5).

In particular, it is thought that the immunostimulatory activity of the compounds of the invention may arise from the stimulation of IL-12 and IL-2 by dendritic cells. This leads to the stimulation of NK cells to produce IFN-γ and induces the development of $CD4^+$ Th1 cells. The induced Th1 cells then produce IFN-γ and IL-2. The IL-2 then enhances further proliferation of Th1 cells and the differentiation of pathogen (e.g. tumour and virus)—specific $CD8^+$ T cells. The IL-2 also stimulates the cytolytic activity of NK cells of the innate immune system.

IL-12 is the primary mediator of type-1 immunity (the Th1 response). It induces natural killer (NK) cells to produce IFN-γ as part of the innate immune response and promotes the expansion of $CD4^+$ Th1 cells and cytotoxic $CD8^+$ cells which produce IFN-γ. It therefore increases T-cell invasion of tumours as well as the susceptibility of tumour cells to T-cell invasion.

Thus, the compounds of the invention are preferably stimulators of cytokine secretion. Particularly preferred are compounds which induce, potentiate, activate or stimulate the release one or more cytokines (for example Th1 cytokines, e.g. IL-12 and/or II-2, optionally together with one or more other cytokines) in vitro.

This primary immunomodulatory activity of the compounds of the invention is particularly important in certain medical applications (discussed in detail infra). For example, increased production of IL-12 may overcome the suppression of innate and cellular immunities of HIV-1-infected individuals and AIDS patients.

The cytokine stimulation exhibited by the compounds of the invention may be dependent, in whole or in part, on the presence of co-stimulatory agents. Such co-stimulatory agents may include, for example, agents that stimulate the innate immune system, including Toll-like receptor (TLR) ligands. These ligands include microbial products such as lipopolysaccharide (LPS) and/or monophosphoryl lipid) as well as other molecules associated with microbial infection. In many applications, such co-stimulatory agents will be present in the patient to be treated at the time of administration of the compounds of the invention.

Without wishing to be bound by any theory, it is thought that at least some of the pharmacological activities of the compounds of the invention may be based on a secondary glycosidase inhibitory activity.

Such glycosidase inhibition may lead to any or all of the following in vivo:

Modification of tumour cell glycosylation (e.g. tumour antigen glycosylation);
Modification of viral protein glycosylation (e.g. virion antigen glycosylation);
Modification of cell-surface protein glycosylation in infected host cells;
Modification of bacterial cell walls.

This ancillary biological activity may therefore augment the primary immunomodulatory activity in some preferred embodiments of the invention. It may be particularly desirable in certain medical applications, including the treatment of proliferative disorders (such as cancer) or in applications where infection is attendant on immune suppression. For example, selective modification of virion antigen glycosylation may render an infecting virus less (or non-) infective and/or more susceptible to endogenous immune responses. In particular, the compounds of the invention may alter the HIV viral envelope glycoprotein gp120 glycosylation patterns, hence inhibiting the entry of HIV into the host cell by interfering with the binding to cell surface receptors.

Thus, the compounds of the invention are preferably (but not necessarily) glycosidase inhibitors. Particularly preferred are compounds which exhibit specificity of glycosidase inhibition, for example Glucosidase I rather than mannosidases. Such preferred compounds can therefore be quite different in their glycosidase inhibitory profile to swainsonine and its analogues, since the latter are potent and specific inhibitors of mannosidase.

Medical Applications of the Compounds of the Invention

The invention finds broad application in medicine, for example in methods of therapy, prophylaxis and/or diagnosis.

These medical applications may be applied to any warm-blooded animal, including humans. The applications include veterinary applications, wherein the pyrrolizidine compounds of the invention are administered to non-human animals, including primates, dogs, cats, horses, cattle and sheep.

The pyrrolizidine compounds of the invention are immunomodulators. Thus, they find general application in the treatment or prophylaxis of conditions in which stimulation, augmentation or induction of the immune system is indicated and/or in which suppression or elimination of part or all of the immune response is indicated.

Particular medical uses of the pyrrolizidine compounds of the invention are described in detail below. References to therapy and/or prophylaxis in the description or claims are to be interpreted accordingly and are intended to encompass inter alia the particular applications described below.

1. Increasing the Th1:Th2 Response Ratio

General Considerations

As explained earlier, the immune response comprises two distinct types: the Th1 response (type-1, cellular or cell mediated immunity) and Th2 response (type-2, humoral or antibody mediated immunity).

These Th1 and Th2 responses are not mutually exclusive and in many circumstances occur in parallel. In such circumstances the balance of the Th1/Th2 response determines the nature (and repercussions) of the immunological defence (as explained herein).

The Th1/Th2 balance (which can be expressed as the Th1:Th2 response ratio) is determined, at least in part, by the nature of the environment (and in particular the cytokine milieu) in which antigen priming of naïve helper T cells occurs when the immune system is first stimulated.

The Th1 and Th2 responses are distinguished inter alia on the basis of certain phenotypic changes attendant on priming and subsequent polarization of naïve helper T cells. These phenotypic changes are characterized, at least in part, by the nature of the cytokines secreted by the polarized helper T cells.

Th1 cells produce so-called Th1 cytokines, which include one or more of IL-1, TNF, IL-2, IFN-gamma, IL-12 and/or IL-18. The Th1 cytokines are involved in macrophage activation and Th1 cells orchestrate cell-mediated defences (including cytotoxic T lymphocyte production) that form a key limb of the defence against bacterial and viral attack, as well as malignant cells.

Th2 cells produce so-called Th2 cytokines, which include one or more of IL-4, IL-5, IL-10 and IL-13. The Th2 cytokines promote the production of various antibodies and can suppress the Th1 response.

Accordingly, in the mouse, a cell that makes IFN-gamma and not IL4 is classified as Th1, whereas a CD4$^+$ cell that expresses IL-4 and not IFN-gamma is classified as Th2. Although this distinction is less clear in humans (T cells that produce only Th1 or Th2 cytokines do not appear to exist in humans), the phenotype of the T cell response (Th1 or Th2) can still be distinguished in humans on the basis of the ratio of Th1 to Th2 cytokines expressed (usually, the ratio of IFN-gamma to IL-4 and/or IL-5).

There is an increasing realization that the type of immune response is just as important in therapy and prophylaxis as its intensity or its duration. For example, an excess Th1 response can result in autoimmune disease, inappropriate inflammatory responses and transplant rejection. An excess Th2 response can lead to allergies and asthma. Moreover, a perturbation in the Th1:Th2 ratio is symptomatic of many immunological diseases and disorders, and the development of methods for altering the Th1:Th2 ratio is now a priority.

It has now been discovered that the immunomodulatory pyrrolizidine compounds of the invention can increase the Th1:Th2 response ratio in vivo (for example, by preferentially promoting a Th1 response and/or preferentially suppressing a Th2 response).

Thus, the compounds of the invention find application in methods of therapy and/or prophylaxis which comprise increasing the Th1:Th2 response ratio (for example, by preferentially promoting a Th1 response and/or preferentially suppressing a Th2 response).

The medical applications contemplated herein therefore include any diseases, conditions or disorders in which an increase in the Th1:Th2 response ratio is indicated or desired. For example, the medical applications contemplated include diseases, conditions or disorders in which stimulation of a Th1 response and/or suppression of a Th2 response is indicated or desired.

The mechanism(s) by which the compounds of the invention increase the Th1:Th2 response ratio are not yet fully understood. It is likely that the activity is based, at least in part, on selective Th1 cytokine induction (since Th1 and Th2 cytokines exhibit mutual inhibition), for example in dendritic cells.

For example, the compounds of the invention may induce, potentiate, activate or stimulate (either directly or indirectly) the release and/or activity (in vitro and/or in vivo) of one or more Th1 cytokines (for example one or more cytokines selected from IFN-gamma, IL-12, IL-2 and IL-18). Particularly preferred are compounds which induce, potentiate, activate or stimulate the release and/or activity (in vitro and/or in vivo) of IFN-gamma and/or IL-12 and/or IL-2.

Particularly preferred are compounds that stimulate the release of IL-2 and IL-12 in dendritic cells.

The compounds of the invention may also suppress or inactivate (either directly or indirectly) the release and/or activity (in vitro and/or in vivo) of one or more Th2 cytokines (for example one or more cytokines selected from IL-4, IL-5, IL-10 and IL-13). Particularly preferred are compounds which suppress or inactivate the release and/or activity (in vitro and/or in vivo) of IL-5.

Thus, particularly preferred are compounds which exhibit a Th-1 cytokine stimulatory activity together with a complementary Th2 cytokine inhibitory activity.

Specific examples of applications falling within the general class of treatments based on increasing the Th1:Th2 response ratio are described in the following sections.

Th1-Related Diseases

Th1-related diseases are diseases, disorders, syndromes, conditions or infections in which Th1 cells are involved in preventing, curing or alleviating the effects of the disease, disorder, syndrome, condition or infection.

Th1-related diseases may also include diseases, disorders, syndromes, conditions or infections in which the Th1 component of the immune response is pathologically depressed or diseases, disorders, syndromes, conditions or infections in which stimulation of a Th1 response is indicated.

Such conditions may arise, for example, from certain proliferative disorders (typically cancers) in which the proliferating (e.g. tumour) cells exert a suppressive effect on one or more components of the Th1 response. For example, tumour cells may inhibit dendritic cells, cause the expression of inhibitory receptors on T cells, down regulate MHC class I expression and induce the secretion of anti-inflammatory factors and immunosuppressive cytokines which deactivate or suppress immune cell cytotoxicity.

Thus, the compounds of the invention find application in the treatment or prophylaxis of Th1-related diseases.

Examples of Th1-related diseases include infectious diseases (particularly viral infections) and proliferative disorders (e.g. cancer).

Thus, the Th1-related diseases include any malignant or pre-malignant condition, proliferative or hyper-proliferative condition or any disease arising or deriving from or associated with a functional or other disturbance or abnormality in the proliferative capacity or behaviour of any cells or tissues of the body.

Thus, the invention finds application in the treatment or prophylaxis of breast cancer, colon cancer, lung cancer and prostate cancer. It also finds application in the treatment or prophylaxis of cancers of the blood and lymphatic systems (including Hodgkin's Disease, leukemias, lymphomas, multiple myeloma, and Waldenstrom's disease), skin cancers (including malignant melanoma), cancers of the digestive tract (including head and neck cancers, cesophageal cancer, stomach cancer, cancer of the pancreas, liver cancer, colon and rectal cancer, anal cancer), cancers of the genital and urinary systems (including kidney cancer, bladder cancer, testis cancer, prostate cancer), cancers in women (including breast cancer, ovarian cancer, gynecological cancers and choriocarcinoma) as well as in brain, bone carcinoid, nasopharyngeal, retroperitoneal, thyroid and soft tissue tumours. It also finds application in the treatment or prophylaxis of cancers of unknown primary site.

The Th1-related infectious diseases include bacterial, prion (e.g. BSE and CJD), viral, fungal, protozoan and metazoan infections. For example, the Th1-related infectious diseases include infection with respiratory syncytial virus (RSV), hepatitis B virus (HBV), Epstein-Barr, hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), tuberculosis, leprosy and measles.

Particularly preferred Th1-related infectious diseases include those in which the pathogen occupies an intracellular compartment, including HIV/AIDS, leishmaniasis, trypanosomiasis, influenza, tuberculosis and malaria.

The compounds of the invention may also find application in the treatment of patients in which the Th1 immune response is defective. Such patients may include neonates, juveniles in which the Th1 response is immature and not fully developed, as well as older patients in which the Th1 response has become senescent or compromised over time. In such patient populations the compounds of the invention may be used prophylactically (as a generalized type 1 immune stimulant to reduce the risks of (e.g. viral) infections.

Th2-Related Diseases and Allergy

Th2-related diseases are diseases, disorders, syndromes, conditions or infections in which Th2 cells are implicated in (e.g. support, cause or mediate) the effects of the disease, disorder, syndrome, condition or infection.

Thus, the compounds of the invention find application in the treatment or prophylaxis of Th2-related diseases.

One important class of Th2-related diseases treatable with the compounds of the invention is allergic disease.

It is well known that genetically predisposed individuals can become sensitised (allergic) to antigens originating from a variety of environmental sources. The allergic reaction occurs when a previously sensitised individual is re-exposed to the same or to a structurally similar or homologous allergen. Thus, as used herein the term allergy is used to define a state of hypersensitivity induced by exposure to a particular antigen (allergen) resulting in harmful and/or uncomfortable immunologic reactions on subsequent exposures to the allergen.

The harmful, uncomfortable and/or undesirable immunologic reactions present in allergy include a wide range of symptoms. Many different organs and tissues may be affected, including the gastrointestinal tract, the skin, the lungs, the nose and the central nervous system. The symptoms may include abdominal pain, abdominal bloating, disturbance of bowel function, vomiting, rashes, skin irritation, wheezing and shortness of breath, nasal running and nasal blockage, headache and mood changes. In severe cases the cardiovascular and respiratory systems are compromised and anaphylactic shock leads in extreme cases to death.

It is known that the harmful, undesirable and/or uncomfortable immunologic reactions characteristic of allergy have a Th2 response component.

As explained above, the compounds of the invention may suppress or inactivate (either directly or indirectly) the release and/or activity (in vitro and/or in vivo) of one or more Th2 cytokines (for example one or more cytokines selected from IL-4, IL-5, IL-10 and IL-13). Thus, the compounds of the invention may be used to effect a remedial or palliative modulation of the harmful and/or uncomfortable immunologic reactions characteristic of allergic reactions by inhibiting, suppressing or eliminating the Th2 response to the allergen.

The compounds of the invention therefore find application in the treatment or prophylaxis of allergy.

Any allergy may be treated according to the invention, including atopic allergy, allergic rhinitis, allergic conjunctivitis, atopic dermatitis, hypereosinophilia, irritable bowel syndrome, allergen-induced migraine, bacterial allergy, bronchial allergy (asthma), contact allergy (dermatitis), delayed allergy, pollen allergy (hay fever), drug allergy, sting allergy, bite allergy, gastrointestinal or food allergy (including that associated with inflammatory bowel disease, including ulcerative colitis and Crohn's disease) and physical allergy. Physical allergies include cold allergy (cold urticaria or angioedema), heat allergy (cholinergic urticaria) and photosensitivity.

Particularly important is the treatment or prophylaxis of asthma.

2. Haemorestoration

The pyrrolizidine compounds of the invention increase splenic and bone marrow cell proliferation and can act as myeloproliferative agents. They therefore find application as haemorestoratives.

Haemorestoration may be indicated following immunosuppressant therapies (such as cyclosporine A, azathioprine or immunosuppressant radiotherapies), chemotherapy (including treatment with both cycle-specific and non-specific chemotherapeutic agents), steroid administration or other forms of surgical or medical intervention (including radiotherapy). Thus, the use of the pyrrolizidine compounds of the invention as haemorestoratives may be adjunctive to other treatments which tend to depress splenic and bone marrow cell populations. Particularly preferred adjunctive therapies according to the invention include the administration of an immunorestorative dose of the pyrrolizidine compound of the invention adjunctive to: (a) chemotherapy; and/or (b) radiotherapy; and/or (c) bone marrow transplantation; and/or (d) haemoablative immunotherapy.

3. Alleviation of Immunosuppression

The pyrrolizidine compounds of the invention may be used to alleviate, control or modify states in which the immune system is partially or completely suppressed or depressed. Such states may arise from congenital (inherited) conditions, be acquired (e.g. by infection or malignancy) or induced (e.g. deliberately as part of the management of transplants or cancers).

Thus, the pyrrolizidine compounds of the invention may find application as adjunctive immunomodulators (e.g. immunostimulants) in the treatment and/or management of various diseases (including certain cancers) or medical interventions (including radiotherapy, immunosuppressant therapy (such as the administration of cyclosporine A, azathioprine or immunosuppressant radiotherapies), chemotherapy and cytotoxic drug administration (for example the administration of ricin, cyclophosphamide, cortisone acetate, vinblastine, vincristine, adriamycin, 6-mercaptopurine, 5-fluorouracil, mitomycin C, chloramphenicol and other steroid-based therapies). They may therefore be used as chemoprotectants in the management of various cancers and infections (including bacterial and viral infections, e.g. HIV infection) or to induce appropriate and complementary immunotherapeutic activity during conventional immunotherapy.

In particular, the pyrrolizidine compounds of the invention may find application as immunostimulants in the treatment or management of microbial infections which are associated with immune-suppressed states, including many viral infections (including HIV infection in AIDS) and in other situations where a patient has been immunocompromised (e.g. following infection with hepatitis C, or other viruses or infectious agents including bacteria, fungi, and parasites, in patients undergoing bone marrow transplants, and in patients with chemical or tumor-induced immune suppression).

Other diseases or disorders which may give rise to an immunosuppressed state treatable according to the invention include: ataxia-telangiectasia; DiGeorge syndrome; Chediak-Higashi syndrome; Job syndrome; leukocyte adhesion defects; panhypogammaglobulinemia (e.g. associated with Bruton disease or congenital agammaglobulinemia); selective deficiency of IgA; combined immunodeficiency disease; Wiscott-Aldrich syndrome and complement deficiencies. It may be associated with organ and/or tissue (e.g. bone marrow) transplantation or grafting, in which applications the pyrrolizidine compounds of the invention may be used adjunctively as part of an overall treatment regimen including surgery and post-operative management of immune status.

4. Cytokine Stimulation

The pyrrolizidine compounds of the invention may be used to induce, potentiate or activate various cytokines in vivo, including various interleukins (including IL-2 and/or IL-12).

Accordingly, the pyrrolizidine compounds of the invention find general application in the treatment or prophylaxis of conditions in which the in vivo induction, potentiation or activation of one or more cytokines (e.g. IL-12 and/or Il-2) is indicated. Such applications may be employed to stimulate particular elements of the cellular immunity system, including dendritic cells, macrophages (e.g. tissue-specific macrophages), CTL, NK, NKT, B and LAK cells.

In such applications, the compounds of the invention may be employed as an adjunct to gene therapies designed to increase the production of endogenous cytokines (for example IL-2).

5. Treatment of Proliferative Disorders

The invention finds application in the treatment of proliferative disorders, including various cancers and cancer metastasis. For example, the pyrrolizidine compounds of the invention may find particular application in the treatment of leukemias, lymphomas, melanomas, adenomas, sarcomas, carcinomas of solid tissues, melanoma (including melanoma of the eye), pancreatic cancer, cervico-uterine cancer, cancers of the kidney, stomach, lung, ovary, rectum, breast, prostate, bowel, gastric, liver, thyroid, neck, cervix, salivary gland, leg, tongue, lip, bile duct, pelvis, mediastinum, urethra, lung, bladder, esophagus and colon, and Kaposi's Sarcoma (e.g. when associated with AIDS).

In such applications the compounds of the invention may exhibit a secondary glycosidase inhibitory activity.

The invention may therefore find application in methods of therapy or prophylaxis which comprise the modification of tumour cell glycosylation (e.g. tumour antigen glycosylation), the modification of viral protein glycosylation (e.g. virion antigen glycosylation), the modification of cell-surface protein glycosylation in infected host cells and/or the modification of bacterial cell walls, hence promoting an increased immune response or inhibiting growth/infectivity directly.

6. Use as Adjuvant

The pyrrolizidine compounds of the invention find utility as vaccine adjuvants, in which embodiments they may promote, induce or enhance an immune response to antigens, particularly antigens having low intrinsic immunogenicity. Without wishing to be bound by any theory, the pyrrolizidine compounds of the invention may augment vaccine immunogenicity by stimulating cytokine release, thereby promoting T-cell help for B cell and CTL responses. They may also change glycosylation of cancer or viral antigens and increase vaccine effectiveness.

When used as adjuvant, the compounds of the invention may be administered concurrently, separately or sequentially with administration of the vaccine. The invention finds application in any vaccine, but may be particularly as a subunit vaccine, a conjugate vaccine, a DNA vaccine, a recombinant vaccine or a mucosal vaccine. The vaccine may be therapeutic or prophylactic. It may be used immunoprophylactically or immunotherapeutically in both human and non-human subjects. Preferred non-human subjects include mammals and birds. Particularly preferred are veterinary applications. Such applications include the treatment or prophylaxis of infection in domesticated animals (for example dogs and cats) and livestock (e.g. sheep, cows, pigs, horses, chickens and turkeys).

Thus, in some embodiments, the pyrrolizidine compound of the invention may be present in admixture with other vaccine component(s), or else co-packaged (e.g. as part of an array of unit doses) with the other vaccine components with which it is to be used as adjuvant. In yet other embodiments, the use of the pyrrolizidine compounds of the invention as adjuvant is simply reflected in the content of the information and/or instructions co-packaged with the vaccine components and relating to the vaccination procedure, vaccine formulation and/or posology.

7. Dendritic Cell-Based Applications

As described above, it has now been found that the pyrrolizidine compounds of the invention may induce sustained and pronounced cytokine production (e.g. sustained and pronounced IL-12 and/or IL-2 production) in dendritc cells. Thus, the compounds of the invention find application in methods of therapy or prophylaxis comprising the induction of cytokine production in dendritic cells or in which the induction of cytokine production in dendritic cells is indicated or required.

Dendritic Cell Vaccines

In one dendritic cell-based treatment paradigm, the cells are pulsed (primed or spiked) with a particular antigen or antigens (for example, tumour antigen(s)) and then administered to promote a Th1 immune response. The responding T cells include helper cells, especially Th1 CD4$^+$ cells (which produce IFN-γ) and killer cells (especially CD8$^+$ cytolytic T lymphocytes). The dendritc cells may also mediate responses by other classes of lymphocytes (B, NK, and NKT cells). They may also elicit T cell memory, a critical goal of vaccination.

With regard to antigen selection for use in the dendritic cell vaccines of the invention, both defined and undefined antigens can be employed. The antigens can be xenoantigens or autoantigens. One or more defined neoantigen(s) may be selected: in the case of cancer treatment, the neoantigen(s) may comprise a tumour-associated antigen.

However, most preferred for use according to the invention are peptides (for example, synthetic 9-11 amino acid peptides) containing defined antigens. Such peptides may comprise natural sequences. Alternatively, they may be synthetic analogues designed for enhanced MHC binding.

In other embodiments, the antigens used according to the invention are provided in the form of immune complexes. These are preferably delivered to Fc-receptor-bearing DCs so that both MHC class I and MHC class II peptide sequences are formed. In this way, dendritic cell vaccines can be used according to the invention for inducing both CTLs and Th cells.

In another approach to antigen selection for use according to the invention, the whole antigenic repertoire of any given tumour (or other target cell, such as a virally-infected cell) is explored. Thus, in another embodiment of the invention there is provided DC-tumour cell hybrids in which the dendritic cells are treated with compound (thereby to induce the expression of IL-2) before or after hybridisation.

In yet other embodiments, necrotic or apoptotic tumour cells or cell lysates (for example lysates of infected cells or tumour cells) are used.

Antigens derived from fresh tumour cells (rather than tumour cell lines or defined antigens) may also be employed.

It is also contemplated that the compounds of the invention be incorporated into cellular antigens by introducing them into the cellular membrane or into an intracellular compartment (as described for example in WO96017614, the contents of which are incorporated herein by reference).

Various techniques can be used to deliver the selected antigen(s) to the DCs (variously referred to in the art as antigen loading, pulsing, priming or spiking). Preferred are loading techniques which load the DCs internally: this can be achieved through the use of peptides linked to cell-penetrating moieties.

Antigens can also be loaded by transfecting the DCs with encoding nucleic acid (e.g. by electroporation) such that the antigens are expressed by the DC, processed and presented at the cell surface. This approach avoids the need for expensive GMP proteins and antibodies. RNA is preferred for this purpose, since it produces only transient expression (albeit sufficient for antigen processing) and avoids the potential problems associated with the integration of DNA and attendant long-term expression/mutagenesis. Such transfection techniques also permit exploration of the whole antigenic repertoire of a target cell by use of total or PCR-amplified tumour RNA.

Current strategies for using dendritic cells in this way focus on identifying specific tumour antigens and defining antigenic peptides that bind to the particular MHC alleles expressed by each patient. However, a more general approach would involve the stimulation of the dendritic cells in a manner appropriate for potentiating Th1 responses irrespective of the antigens present and either with or without antigen priming. Cytokine production by activated dendritic cells would then promote the appropriate Th1 response.

The dendritic cell based vaccines of the invention find particular application in the treatment or prophylaxis of various proliferative disorders (including various cancers, as described below). In such applications, the dendritic cells are preferably pulsed (primed or spiked) with one or more tumour antigens ex vivo and the compounds of the invention used to potentiate the dendritic cell component of the vaccine by contacting the dendritic cells with the compound either ex vivo (before or after pulsing of the cells) or in vivo (for example by co-administration, either concurrently, separately or sequentially, of the dendritic cells and the compound).

The dendritic cell based vaccines of the invention may be used in the treatment or prophylaxis of any malignant or pre-malignant condition, proliferative or hyper-proliferative condition or any disease arising or deriving from or associated with a functional or other disturbance or abnormality in the proliferative capacity or behaviour of any cells or tissues of the body.

Thus, the invention finds application in the treatment or prophylaxis of breast cancer, colon cancer, lung cancer and prostate cancer. It also finds application in the treatment or prophylaxis of cancers of the blood and lymphatic systems (including Hodgkin's Disease, leukemias, lymphomas, multiple myeloma, and Waldenstrom's disease), skin cancers (including malignant melanoma), cancers of the digestive tract (including head and neck cancers, cesophageal cancer, stomach cancer, cancer of the pancreas, liver cancer, colon and rectal cancer, anal cancer), cancers of the genital and urinary systems (including kidney cancer, bladder cancer, testis cancer, prostate cancer), cancers in women (including breast cancer, ovarian cancer, gynecological cancers and choriocarcinoma) as well as in brain, bone carcinoid, nasopharyngeal, retroperitoneal, thyroid and soft tissue tumours. It also finds application in the treatment or prophylaxis of cancers of unknown primary site.

The dendritic cell based vaccines of the invention also find application in the treatment or prophylaxis of various infections, including bacterial, viral, fungal, protozoan and metazoan infections. For example, the vaccines may be used in the treatment or prophylaxis of infection with respiratory syncytial virus (RSV), Epstein-Barr, hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), tuberculosis, leprosy and measles.

Particularly preferred is the treatment or prophylaxis of infections in which the pathogen occupies an intracellular compartment or causes the expression of neoantigens by host cells, including HIV/AIDS, leishmania, trypanosomiasis, influenza, tuberculosis and malaria.

The present invention also contemplates a more general approach to DC cell-based therapy which involves the stimulation of the dendritc cells with the compound of the invention irrespective of the antigens present and either with or without antigen priming.

Thus, the invention finds application in therapies in which dendritic cells exposed to the compound of the invention are targeted to diseased or infected tissue (for example injected directly into a tumour), where the cells can prime endogenous T cells extranodally. In such embodiments, the invention contemplates targeting of DCs to a tumour and their activation in situ to elicit immune responses without the need for ex vivo antigen loading.

In yet another embodiment, the invention contemplates in situ DC vaccination where antigen is targeted to DCs in vivo which are then expanded and induced to mature in situ (by the co-administration of one or more DC maturation stimulants). In such embodiments, antigen is targeted to endogenous DCs by any convenient method, for example through the use of exosomes (as described in Thery et al. (2002) Nat Rev Immunol 2: 569-579).

Any class of dendritic cell may be used according to the invention. Thus, the dendritic cells may be myeloid or lymphoid, or mixtures thereof. The myeloid dendritic cells, if used, may be of the Langerhans cell type or interstitial DCs. Alternatively, mixtures of these myeloid subsets may be used. Especially preferred is the use of monocyte-derived DCs (Mo-DCs).

Helper proteins may be used to potentiate the activity of the dendritic cell vaccines of the invention.

Dendritic Cell-Based Approaches to Autoimmune Disorders

Dendritic cells are also involved in regulating and maintaining immunological tolerance: in the absence of maturation, the cells induce antigen-specific silencing or tolerance. Thus, in another dendritic cell-based treatment paradigm the cells are administered as part of an immunomodulatory intervention designed to combat autoimmune disorders.

In such applications, the suppressive potential of dendritic cells has been enhanced by in vitro transfection with genes encoding cytokines. However, such gene therapy approaches are inherently dangerous and a more efficient and attractive approach would be to pulse dendritic cells in vitro with biologically active compounds which stimulate an appropriate cytokine secretion pattern in the dendritic cells.

As described above, it has now been discovered that the pyrrolizidine compounds of the invention can induce sustained and pronounced cytokine production in dendritic cells. Thus, the compounds of the invention find application in the enhancement of the suppressive potential of dendritic cells.

Thus, the invention finds application in the treatment or prophylaxis of autoimmune disorders, including myasthenia gravis, rheumatoid arthritis, systemic lupus erythematosus, Sjogren syndrome, scleroderma, polymyositis and dermomyositis, ankylosing spondylitis, and rheumatic fever, insulin-dependent diabetes, thyroid diseases (including Grave's disease and Hashimoto thyroidits), Addison's disease, multiple sclerosis, psoriasis, inflammatory bowel disease, ulcerative colitis and autoimmune male and female infertility.

8. Wound Healing

The pyrrolizidine compounds of the invention can reverse a Th2 type splenocyte response ex vivo in a normally non-healing infectious disease model. Antigen specific splenocyte IFN-gamma can be significantly increased and IL-5 production significantly reduced in such models, indicative of a healing response.

Thus, the invention finds application in the treatment of wounds. In particular, the invention finds application in the treatment or prophylaxis of wounds and lesions, for example those associated with post-operative healing, burns, infection (e.g. necrotic lesions), malignancy or trauma (e.g. associated with cardiovascular disorders such as stroke or induced as part of a surgical intervention).

The wound treatments may involve the selective suppression or elimination of a Th2 response (for example to eliminate or suppress an inappropriate or harmful inflammatory response).

Posology

The pyrrolizidine compounds of the present invention can be administered by oral or parenteral routes, including intravenous, intramuscular, intraperitoneal, subcutaneous, transdermal, airway (aerosol), rectal, vaginal and topical (including buccal and sublingual) administration.

The amount of the pyrrolizidine compound administered can vary widely according to the particular dosage unit employed, the period of treatment, the age and sex of the patient treated, the nature and extent of the disorder treated, and the particular pyrrolizidine compound selected.

Moreover, the pyrrolizidine compounds of the invention can be used in conjunction with other agents known to be useful in the treatment of diseases, disorders or infections where immunostimulation is indicated (as described infra) and in such embodiments the dose may be adjusted accordingly.

In general, the effective amount of the pyrrolizidine compound administered will generally range from about 0.01 mg/kg to 500 mg/kg daily. A unit dosage may contain from 0.05 to 500 mg of the pyrrolizidine compound, and can be taken one or more times per day. The pyrrolizidine compound can be administered with a pharmaceutical carrier using conventional dosage unit forms either orally, parenterally, or topically, as described below.

The preferred route of administration is oral administration. In general a suitable dose will be in the range of 0.01 to 500 mg per kilogram body weight of the recipient per day, preferably in the range of 0.1 to 50 mg per kilogram body weight per day and most preferably in the range 1 to 5 mg per kilogram body weight per day.

The desired dose is preferably presented as a single dose for daily administration. However, two, three, four, five or six or more sub-doses administered at appropriate intervals throughout the day may also be employed.

These sub-doses may be administered in unit dosage forms, for example, containing 0.001 to 100 mg, preferably 0.01 to 10 mg, and most preferably 0.5 to 1.0 mg of active ingredient per unit dosage form.

Formulation

The compositions of the invention comprise the pyrrolizidine compound of the invention, optionally together with a pharmaceutically acceptable excipient.

The pyrrolizidine compound of the invention may take any form. It may be synthetic, purified or isolated from natural sources (for example from *Casuarina equisetifolia* or *Eugenia jambolana*), using techniques described in the art (and referenced infra).

When isolated from a natural source, the pyrrolizidine compound of the invention may be purified. However, the compositions of the invention may take the form of herbal medicines, as hereinbefore defined. Such herbal medicines preferably are analysed to determine whether they meet a standard specification prior to use.

The herbal medicines for use according to the invention may be dried plant material. Alternatively, the herbal medicine may be processed plant material, the processing involving physical or chemical pre-processing, for example powdering, grinding, freezing, evaporation, filtration, pressing, spray drying, extrusion, supercritical solvent extraction and tincture production. In cases where the herbal medicine is administered or sold in the form of a whole plant (or part thereof), the plant material may be dried prior to use. Any convenient form of drying may be used, including freeze-drying, spray drying or air-drying.

In embodiments where the pyrrolizidine compound of the invention is formulated together with a pharmaceutically acceptable excipient, any suitable excipient may be used, including for example inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc.

The pharmaceutical compositions may take any suitable form, and include for example tablets, elixirs, capsules, solutions, suspensions, powders, granules and aerosols.

The pharmaceutical composition may take the form of a kit of parts, which kit may comprise the composition of the invention together with instructions for use and/or a plurality of different components in unit dosage form.

Tablets for oral use may include the pyrrolizidine compound of the invention, either alone or together with other plant material associated with the botanical source(s) (in the case of herbal medicine embodiments). The tablets may contain the pyrrolizidine compound of the invention mixed with pharmaceutically acceptable excipients, such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract Capsules for oral use include hard gelatin capsules in which the pyrrolizidine compound of the invention is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity.

Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

For oral administration the pyrrolizidine compound of the invention can be formulated into solid or liquid preparations such as capsules, pills, tablets, troches, lozenges, melts, powders, granules, solutions, suspensions, dispersions or emulsions (which solutions, suspensions dispersions or emulsions may be aqueous or non-aqueous). The solid unit dosage forms can be a capsule which can be of the ordinary hard- or soft-shelled gelatin type containing, for example, surfactants, lubricants, and inert fillers such as lactose, sucrose, calcium phosphate, and cornstarch.

In another embodiment, the pyrrolizidine compounds of the invention are tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient.

Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent or emulsifying agent.

The pyrrolizidine compounds of the invention may also be administered parenterally, that is, subcutaneously, intravenously, intramuscularly, or interperitoneally.

In such embodiments, the pyrrolizidine compound is provided as injectable doses in a physiologically acceptable diluent together with a pharmaceutical carrier (which can be a sterile liquid or mixture of liquids). Suitable liquids include water, saline, aqueous dextrose and related sugar solutions, an alcohol (such as ethanol, isopropanol, or hexadecyl alcohol), glycols (such as propylene glycol or polyethylene glycol), glycerol ketals (such as 2,2-dimethyl-1,3-dioxolane-4-methanol), ethers (such as poly(ethylene-glycol) 400), an oil, a fatty acid, a fatty acid ester or glyceride, or an acetylated fatty acid glyceride with or without the addition of a pharmaceutically acceptable surfactant (such as a soap or a detergent), suspending agent (such as pectin, carnomers, methylcellulose, hydroxypropylmethylcellulose, or carboxymethylcellulose), or emulsifying agent and other pharmaceutically adjuvants. Suitable oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil.

Suitable fatty acids include oleic acid, stearic acid, and isostearic acid. Suitable fatty acid esters are, for example, ethyl oleate and isopropyl myristate.

Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulphonates, alkyl, olefin, ether, and monoglyceride sulphates, and sulphosuccinates; nonionic detergents, for example, fatty amine oxides, fatty acid alkanolamides, and polyoxyethyleneepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5 to about 25% by weight of the pyrrolizidine compound of the invention in solution. Preservatives and buffers may also be used. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pyrrolizidine compounds of the invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the compound from about 0.1 to about 10% w/v (weight per unit volume).

When used adjunctively, the pyrrolizidine compounds of the invention may be formulated for use with one or more other drug(s), in particular, the pyrrolizidine compounds of the invention may be used in combination with antitumor agents, antimicrobial agents, anti-inflammatories, antiproliferative agents and/or other immunomodulatory (e.g. immunostimulatory) agents. For example, the pyrrolizidine compounds of the invention may be used with anti-viral and/or anti-proliferative agents such as cytokines, including interleukins-2 and 12, interferons and inducers thereof, tumor necrosis factor (TNF) and/or transforming growth factor (TGF), as well as with myelosuppressive agents and/or chemotherapeutic agents (such as doxorubicin, 5-fluorouracil, cyclophosphamide and methotrexate), isoniazid (e.g. in the prevention or treatment of peripheral neuropathy) and with analgesics (e.g. NSAIDs) for the prevention and treatment of gastroduodenal ulcers.

Thus, adjunctive use may be reflected in a specific unit dosage designed to be compatible (or to synergize) with the other drug(s), or in formulations in which the pyrrolizidine compound is admixed with one or more antitumor agents, antimicrobial agents and/or antiinflammatories (or else physically associated with the other drug(s) within a single unit dose). Adjunctive uses may also be reflected in the composition of the pharmaceutical kits of the invention, in which the pyrrolizidine compound of the invention is co-packaged (e.g. as part of an array of unit doses) with the antitumor agents, antimicrobial agents and/or antiinflammatories. Adjunctive use may also be reflected in information and/or instructions relating to the co-administration of the pyrrolizidine compound with antitumor agents, antimicrobial agents and/or antiinflammatories.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1

Induction of IL-12 Secretion in Dendritic Cells

Mice

BALB/c male and female mice bred and maintained at the University of Strathclyde under conventional conditions were used at 8 weeks old.

Isolation of Bone Marrow and Culture of Dendritic Cells

Bone marrow was obtained from the femurs of mice. The femurs were washed in 70% ethanol and placed in a 40 clean petri dish. Dendritic cell (DC) medium (2.5% granulocyte-macrophage colony-stimulating factor (GM-CSF), 10% heat and activated foetal calf serum, 1% L-glutamine, 1% Penicillin/Streptomycin in RPMI-1640 medium) was injected into the bone marrow of the femur by a pumping action and the cells and medium were collected. 1 ml of the cells in medium was added to a 75 cm$^2$ flask with 15 mls of DC medium. The flasks were then incubated at 37° C., 5% $CO_2$ to allow DC growth and development. After 5 days an additional 10 mls of DC medium was added.

Harvesting of Dendritic Cells

After 10 days of incubation of bone marrow with GM-CSF, the dendritic cells were harvested. This process was carried out in a tissue culture hood. The contents of the flasks were poured into centrifuge tubes to ensure collection of floating DCs. Approximately 10 mls of cooled phosphate buffered saline (PBS) was added to each empty flask, the flasks gently agitated and the contents collected. This ensured recovery of adhesive DCs. The collected contents of the flasks were centrifuged for 5 minutes at 200 g and the pellet resuspended in 2 mls of DC medium without GM-CSF. A cell count was then carried out.

Cell Count and Assay Conditions

Cells were counted using a haemocytometer. Approximately 20 μl of the resuspended cells was pipetted into the chamber of the haemocytometer, the cells were adjusted to the correct cell concentration (approx. 5×10$^4$ and not less than 1×10$^4$, per well) and then plated out for assay.

The plates were incubated overnight at 37° C. with 5% $CO_2$ and allowed to settle (harvesting stimulates them). The next day the compounds (50 μg/ml and 20 μg/ml) and controls were added then again incubated at 37° C. with 5% $CO_2$ for 24 hrs (or 48 hrs). Harvesting and addition of the compounds was all done in a hood. The plates were then frozen to kill the cells and once defrosted the supernatant analysed as described below.

Measurement of IL-12

Using an enzyme linked immunosorbent assay (ELISA) IL-12 concentration in the supernatants was measured. All reagents used in this assay were from PharMingen. A 96-well flat-bottomed ELISA plate was coated with purified rat anti-mouse IL-12 (p40/p70) MAb (Cat no. 554478) at 2 μg/ml diluted in PBS pH 9.0 at 50 μl/well. The plate was then covered in cling film and incubated at 4° C. Following incubation the plate was washed 3 times in washing buffer and dried. 200 μl of blocking buffer (10% foetal calf serum in PBS pH 7.0) was added to each well then covered in cling film and incubated at 37° C. for 45 minutes. The plate was washed 3 times and dried. Recombinant mouse Il-12 standard was added at 30 μl in duplicate wells, starting at 10 ng/ml then 5, 2.5, 1.25, 0.625, 0.31, 0.156, 0.078, 0.039, 0.020, 0.010, 0.005 ng/ml. Standards were diluted in blocking buffer. The supernatant samples were added in at 50 μl/well. The plate was then covered in cling film and incubated for 2 hours at 37° C. The plate was then washed 4 times, dried and the secondary antibody added.

Biotin labeled anti-mouse IL-12 (p40/p70) MAb (Cat no. 18482D) at 1 μg/ml (diluted in blocking buffer) was added to each well at a volume of 100 μl/well. The plate was covered in cling film and incubated at 37° C. for 1 hour. The plate was then washed 5 times, dried and the conjugate added. Streptavidin-AKP (Cat no. 13043E) at 100 μl/well was added at a dilution of 1/2000 in blocking buffer followed by incubation under cling film at 37° C. for 45 minutes.

The plate was finally washed 6 times, dried and the substrate added: pNPP (Sigma) in glycine buffer at 1 mg/ml was added at 100 μl/well. The plate was then covered in tinfoil, incubated at 37° C. and checked every 30 minutes for a colour change.

Figure 2:
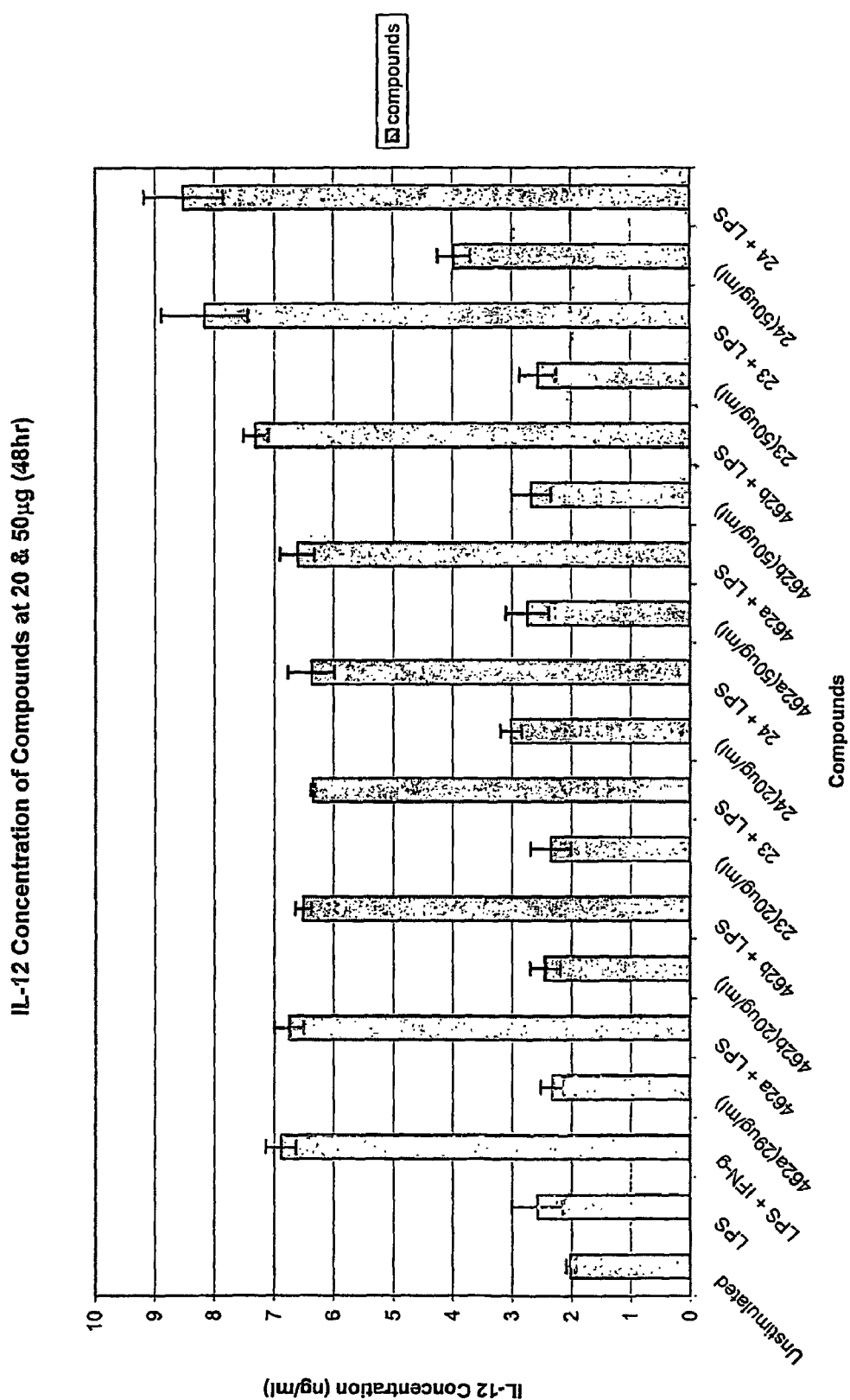
FIG. 2 shows IL-12 concentrations after treatment with some embodiments of the invention at 48 hours in an enzyme linked immunosorbent assay (ELISA).

The plate was then read at 405 nm using a SPECTRAmax 190 spectrometer. The results are shown in FIGS. 1 and 2, in which LPS is lipopolysaccharide, IFN-g is interferon gamma, 462a is casuarine (8), 462b is casuarine-6-α-D-glucopyranose (9), 23 is 7-epicasuarine (11) and 24 is 3,7-diepi-casuarine (10).

When tested at 50 μg/ml in the same assay, swainsonine (4) failed to induce IL-12 secretion. Similar studies with other compounds for comparative purposes are shown in Table 1.1, below.

| COMPOUND | STRUCTURE | IL-12 RELEASE |
|---|---|---|
| casuarine (8) | [structure] | Yes |
| casuarine-6-α-D-glucopyranose (9) | [structure] | Yes |
| 3,7-diepi-casuarine (10) | [structure] | Yes |
| 7-epi-casuarine (11) | [structure] | Yes |
| 3-epi-casuarine (14) | [structure] | Yes |

-continued

| COMPOUND | STRUCTURE | IL-12 RELEASE |
|---|---|---|
| Castanospermine (20) | 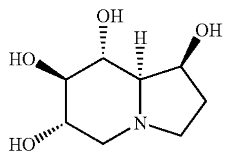 [SMILES: O[C@H]1[C@H](O)[C@@H](O)CN2CC[C@H](O)[C@H]12] | No |
| Swainsonine (4) | 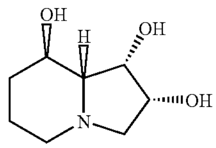 [SMILES: O[C@H]1[C@H]2[C@H](O)CCCN2C[C@H]1O] | No |
| 1-Deoxynojirimycin (DNJ) (21) | 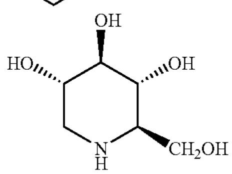 | No |
| 7-epialexine (22) | 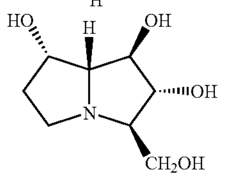 | No |
| 3,7a-diepialexine (23) | 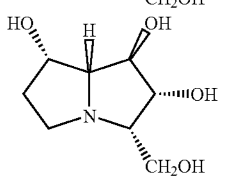 | No |
| Alexine (1) | 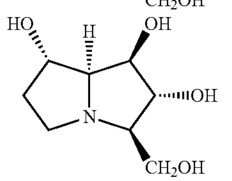 | No |

Example 2

Stimulation of IL-2 Production by Dendritic Cells

The protocols described in Example 1 above were carried out but the appropriate Mabs and standards for determination of Il-2 were substituted. The results are shown in Table 2.1, below.

| Treatment | IL-2 (units/ml) |
|---|---|
| LPS | 0.00 |
| LPS + IFN-$\gamma$ | 0.00 |
| 3,7-diepi-casuarine (10) | 0.00 |
| 3,7-diepi-casuarine (10) + LPS | 0.69 |

Example 3

Cytokine Modulation in Spleen Cells

Mice

BALB/c male and female mice bred and maintained at the University of Strathclyde under conventional conditions were used at varying age.

Isolation of Spleen Cells and Culture of Spleen Cells

The mouse spleen was removed aseptically and placed in a sterile petri dish containing 5 mls of complete medium (RPMI, 1% L-Glutamine, 1% Penicillin/Streptomycin and 10% foetal calf serum). Cells suspensions were prepared by using the end of a syringe and grinding the spleen through a wire mesh. The cell suspension was then centrifuged at 1000 rpm for 5 minutes. To remove the erythrocytes, the cell pellet was resuspended in Boyle's solution (Tris 0.17M Ammonium Chloride 0.16M) and centrifuged again for 5 minutes. The pellet was then washed in medium a further two times, then resuspended in 3 mls medium. A cell count was then carried out.

Experimental Protocol

All spleen cell experiments were carried out in 96-well tissue culture plates. 100 μl aliquots of $5 \times 10^5$/well cells were added to all wells and each well had a final volume of 200 μl. Unstimulated wells contained 100 μl of cells and 100 μl of medium. The stimulated wells contained 100 μl of cells plus 50 μl of LPS at 1 μg/ml or 50 μl anti-CD3 at 0.5 μg/ml and 50 μl of medium. The remaining wells contained 100 μl cells, 50 μl of MNLP compound and either 50 μl of anti-CD3 or medium alone.

Measurement of IL-12, IL-2, IL-5 and IFN-$\gamma$

The appropriate Mabs and standards were used according to the protocol described for IL-12 (described in Example 1, above). The results are shown in Tables 3.1-3.3, below.

TABLE 3.1

Promotion of activated splenocyte (T-cell) IFN-$\gamma$ production

| Treatment | IFN-$\gamma$ $_{(ng/ml)}$ |
|---|---|
| None (control) | 0.64 |
| $\alpha$CD3 | 3.21 |
| 3,7-diepi-casuarine (10) | 0.22 |
| 3,7-diepi-casuarine (10) + $\alpha$CD3 | 13.50 |

TABLE 3.2

Effect of castanospermine on splenocyte IFN-$\gamma$ production

| Treatment | IFN-$\gamma$ $_{(ng/ml)}$ |
|---|---|
| None (control) | <1.0 |
| $\alpha$CD3 | 22.5 |
| Castanospermine (20) | <1.0 |
| Castanospermine (20) + aCD3 | 9.0 |

As can be seen from the results shown in Tables 3.1 and 3.2, compounds according to the invention stimulate IFN-$\gamma$ secretion/production in splenocytes, whereas castanospermine inhibits the production of this cytokine in such assays. Similar tests carried out with 1-Deoxynojirimycin (DNJ) (21) showed that this imino sugar also inhibited IFN-$\gamma$ secretion/production in splenocytes (data not shown).

Example 4

Inhibition of Glycosidase Activity

All enzymes were purchased from Sigma, as were the appropriate p-nitrophenyl substrates. Assays were carried out in microtitre plates. Enzymes were assayed in 0.1M citric acid/0.2M di-sodium hydrogen phosphate (McIlvaine) buffers at the optimum pH for the enzyme. All assays were carried out at −20° C. For screening assays the incubation assay consisted of 10 μl of enzyme solution, 10 μl of inhibitor solution (made up in water) and 50 μl of the appropriate 5 mM p-nitrophenyl substrate (3.57 mM final conc.) made up in McIlvaine buffer at the optimum pH for the enzyme.

The reactions were stopped with 0.4M glycine (pH 10.4) during the exponential phase of the reaction, which was determined at the beginning of the assay using blanks with water, which were incubated for a range of time periods to measure the reaction rate using 5 mM substrate solution. Endpoint absorbances were read at 405 nm with a Biorad microtitre plate reader (Benchmark). Water was substituted for the inhibitors in the blanks.

The enzymes tested are shown in Table 4.1, below.

| Enzyme | Source | pH | Conc. | Substrate |
|---|---|---|---|---|
| α-D glucosidase | *Saccharomyces cerevisiae* (Baker's yeast), rice (*Oryza sativa*), *Bacillus stearothermophilus* | 6.0 | 0.1 unit/ml | PNP-α-D-glucopyranoside |
| β-D-glucosidase | Almonds (*Prunus* sp.) | 5.0 | 0.2 unit/ml | PNP-β-D-glucopyranoside |
| α-D-galactosidase | Green coffee beans (*Coffea* sp.) | 6.5 | 1 unit/ml | PNP-α-D-galactopyranoside |
| β-D-galactosidase | Bovine liver | 7.3 | 0.1 unit/ml | PNP-β-D-galactopyranoside |
| α-D-mannosidase | Jack beans (*Canavalia ensiformis*) | 4.5 | 0.1 unit/ml | PNP-α-D-mannopyranoside |
| α-L-fucosidase | Bovine kidney | | | |
| N-acetyl-β-D-glucosaminidase | Bovine kidney | 4.2 5 | 0.1 unit/ml | PNP-N-acetyl-β-D-glucosminide |
| Naringinase | *Penecillium decumbens* | 4.0 | 1 unit/ml | PNP-α-L-rhamnopyranoside |

The compounds tested are shown in Table 4.2, below.

| Compound name | Structure | Reference |
|---|---|---|
| Castanospermine | | 20 |
| Swainsonine | | 4 |
| Casuarine | | 8 |
| 3,6,7-triepi-casuarine | 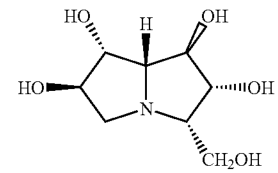 [SMILES: OC[C@H]1[C@@H](O)[C@H](O)[C@H]2[C@@H](O)[C@H](O)CN21] | 12 |
| 3,6,7,7a-tetraepi-casuarine | 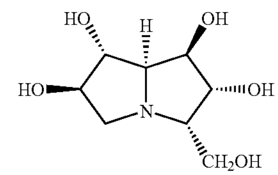 [SMILES: OC[C@H]1[C@@H](O)[C@H](O)[C@@H]2[C@@H](O)[C@H](O)CN21] | 21 |
| 3,7,7a-triepi-casuarine | 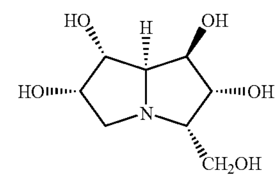 [SMILES: OC[C@H]1[C@@H](O)[C@H](O)[C@@H]2[C@@H](O)[C@@H](O)CN21] | 22 |
| 3-epi-casuarine | 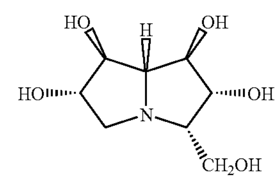 [SMILES: OC[C@H]1[C@@H](O)[C@H](O)[C@H]2[C@H](O)[C@@H](O)CN21] | 14 |
| 3,7-diepi-casuarine | 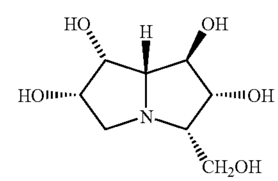 [SMILES: OC[C@H]1[C@@H](O)[C@H](O)[C@H]2[C@@H](O)[C@@H](O)CN21] | 10 |
| 7-epi-casuarine | 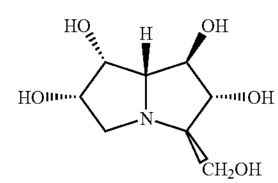 | 11 |

The results (% inhibition) for a number of different compounds (all at 1 mg/ml) are shown in Table 4.3, below:

| | Compound | | | | | | | | |
|---|---|---|---|---|---|---|---|---|---|
| Enzyme | 20 | 4 | 8 | 12 | 21 | 22 | 14 | 10 | 11 |
| gluc (yeast) | −8 | nd | 64 | 2 | −1 | 29 | 0 | −2 | 11 |
| gluc (rice) | 77 | nd | 76 | 0 | 46 | 0 | 13 | 7 | 73 |
| gluc (*Bacillus*) | 6 | nd | 86 | 9 | −2 | 87 | 12 | −7 | 5 |
| glucosidase | 88 | nd | 0 | 6 | 44 | 52 | 56 | 5 | 30 |
| galactosidase | −3 | nd | 4 | 2 | −3 | −2 | 4 | −11 | 1 |
| galactosidase | 16 | nd | 0 | 6 | 3 | 52 | 6 | 24 | 35 |
| mannosidase | 9 | 74 | 5 | 8 | 1 | −1 | −4 | 8 | 10 |
| fucosidase | 3 | nd | −1 | −11 | nd | nd | −2 | 5 | 25 |
| Naringinase | 39 | nd | −2 | 0 | 5 | 10 | 21 | 6 | −4 |
| N-acetyl-β-gluc | 16 | nd | 14 | 19 | 27 | 11 | −1 | −6 | 11 |

The results show that the profile of inhibition for the compounds of the invention is quite different from that of castanospermine. None inhibits mannosidase significantly (see also further data below). Some of the compounds tested (e.g. 3,7-diepi-casuarine) do not significantly inhibit any of the enzymes tested.

Further studies showed that the $K_i$ for casuarine (8) with yeast α-D-glucosidase was 217 μM (castanospermine not being inhibitory at a concentration of 800 μM). The $K_i$ for castanospermine (20) with almond β-D-glucosidase was 9 μM (casuarine not being inhibitory at 800 μM). Moreover, casuarine also inhibited rabbit gut mucosa α-D-glucosidase with an $IC_{50}$ value of 210 μM, as compared with an $IC_{50}$ value of 8 μM for castanospermine. Both casuarine and castanospermine inhibited rabbit small intestine sucrose at a concentration of 700 μM. Castanospermine also inhibited rabbit small intestine lactase and trehalase by over 50% at this concentration.

Example 5

Differential Inhibition of Mannosidase and Glucosidase

The glycosidase inhibitory profiles of swainsonine (45), casuarine (8) and casuarine glucoside (9) with respect to a mannosidase and a glucosidase were compared. The results (all at <0.1 mg/ml) are shown in Table 5.1, below.

| Compound | Mannosidase inhibition | Glucosidase I inhibition |
|---|---|---|
| Swainsonine (4) | + | − |
| Casuarine (8) | − | + |
| Casuarine glucoside (9) | − | + |

Example 6

Treatment of Murine HSV-1 Infection

Mice were 3-4 weeks old female BALB/c. Mice were inoculated with $10^4$ p.f.u. HSV-1 (SC16) using the neck skin method. This dose is sublethal but produces clinical symptoms, including inflammation (measured by increase in ear pinna thickness).

Mice were administered (100 ml i.p.) with one of two doses of casuarine (8) on day one and daily thereafter for 5 days. Group 1 received 15 mg/kg in PBS, group 2 received 150 mg/kg in PBS. A negative control group 3 were infected but received no casuarine. A positive control group 4 were administered with famciclovir (via drinking water spiked at 1 mg/ml for the same time period).

Mice were checked daily and samples were obtained from mice killed on selected days. The results are presented in Tables 6.1-6.3, below.

TABLE 6.1

| | Weight (% change) Group | | | |
|---|---|---|---|---|
| Day | 1 | 2 | 3 | 4 |
| −2 | 0 | 0 | 0 | 0 |
| −1 | | | | |
| 0 | 3.1 | 3.2 | 1.3 | 9 |
| 1 | 5.6 | 5.8 | 4.6 | 13 |
| 2 | 5.6 | 5.2 | 6.5 | 14.5 |
| 3 | 8.6 | 7.1 | 9.3 | 18.8 |

TABLE 6.1-continued

| | Weight (% change) Group | | | |
|---|---|---|---|---|
| Day | 1 | 2 | 3 | 4 |
| 4 | 7.4 | 5.8 | 9.8 | 18.1 |
| 5 | 8.6 | 8.4 | 10.5 | 21 |
| 6 | 9.2 | 9.7 | 12.4 | 23.9 |
| 7 | 7.4 | 7.7 | 11.1 | 21 |
| 8 | 9.3 | 8.4 | 13.7 | 23.9 |

TABLE 6.2

| | Group mean weight (g) Group | | | |
|---|---|---|---|---|
| Day | 1 | 2 | 3 | 4 |
| −2 | 16.2 | 15.5 | 15.3 | 13.8 |
| −1 | | | | |
| 0 | 16.7 | 16 | 15.5 | 15.1 |
| 1 | 17.1 | 16.4 | 16 | 15.6 |
| 2 | 17.1 | 16.3 | 16.3 | 15.8 |
| 3 | 17.6 | 16.6 | 16.7 | 16.4 |
| 4 | 17.4 | 16.4 | 16.8 | 16.3 |
| 5 | 17.6 | 16.8 | 16.9 | 16.7 |
| 6 | 17.7 | 17 | 17.2 | 17.1 |
| 7 | 17.4 | 16.7 | 17 | 16.7 |
| 8 | 17.7 | 16.8 | 17.4 | 17.1 |
| 9 | | | 17.3 | 17.1 |
| 10 | | | 17.4 | 17.2 |
| 11 | | | 17.3 | 17.1 |
| 12 | | | 17.3 | 17.2 |

TABLE 6.3

| | Ear pinna thickness ($mm^{-2}$) Group | | | |
|---|---|---|---|---|
| Day | 1 | 2 | 3 | 4 |
| −2 | 0 | 0 | 0 | 0 |
| −1 | | | | |
| 0 | 0.7 | 0.7 | 2.2 | 0 |
| 1 | 0 | 3.6 | 4.4 | 0 |
| 2 | 13.9 | 23.4 | 14.7 | 0 |
| 3 | 9 | 5.7 | 17.7 | 7 |
| 4 | 9 | 9.2 | 26.5 | 7 |
| 5 | 7.6 | 2.1 | 12.5 | 0 |
| 6 | 12.5 | 14.9 | 13.2 | 4 |
| 7 | 6.2 | 0 | 11 | 0 |
| 8 | 0 | 12.1 | 6.6 | 2.9 |
| 9 | | | 11.8 | 2.9 |
| 10 | | | 14 | 10.7 |
| 11 | | | 11 | 2.9 |
| 12 | | | 7.4 | 12.9 |
| 13 | | | 16.2 | 12.9 |

The results show the expected pattern of ear pinna thickness increase, peaking at day 4. Famvir almost completely negated the ear thickness response. Casuarine at both doses tested also produced a reduction in ear thickness.

Example 7

Control of Lung Metastasis in Mice

Mice (C57/bl6 under i/p ketamine anaesthesia) were challenged i/v (tail vein) with $5 \times 10^4$ B16-F10 tumour cells in a final volume of 100 μl per mouse on day 0. Test compounds (50 mg/kg in 200 μl sterile non-pyrogenic saline) were administered s/c (right flank) on days 2 and 4. On day 14 the mice were sacrifices and the lungs dissected and stained in Indian ink solution (150 ml bidistilled water, 30 ml India Ink, 4 drops NH$_4$OH) for 10 minutes then fixed for at least 24 hr in Fakete's solution (90 ml 37% formaldehyde, 900 ml 70% EtOH and 45 ml glacial acetic acid). The metastases in the stained and fixed lungs could then be visualized, counted and photographed.

The results are shown below in Table 7.1, below.

| Compound | Metastatic morphology |
|---|---|
| PBS (control) | Metastasis over entire lung surface |
| casuarine (8) | Metastasis restricted to apical tip of lung |
| 3-epi-casuarine (14) | Metastasis restricted to apical tip of lung |

Example 8

Effect on Glycosylation of Breast Cancer Cells

Cell Culture

MCF-7 cells (European Collection of Cell Cultures Ref. 86012803) were taken from liquid nitrogen stock, thawed at room temperature and transferred to 10 ml Dulbeccos Modified Eagle's Medium with Hams F12, 15 mM Hepes and L-glutamine (DMEM: Cambrex. Cat. No. BE12-719F) supplemented with 10% v/v foetal calf serum (FCS: BioWest Labs Cat. No. S02755, Lot. No. S1800). The FCS was pre-filtered through a 0.2 μm sterile filter.

The cells were then centrifuged at 1,500 rpm in a Centaur bench-top centrifuge and the supernatant removed. The cells were reconstituted in fresh media and seeded into two T75 cm$^3$ Nunclon tissue culture flasks and allowed to settle overnight at 37° C. in a 5% CO$_2$ incubator. The flasks were wrapped in cling film to prevent cross-contamination and the following day the media was changed to include the antibiotics penicillin and streptomycin as a precautionary measure against infection (at concentrations of 1 mg/cm$^3$ and 5 mg/cm$^3$, respectively).

The cells were allowed to grow near confluence and then split at a 1 in 4 resuspension. The cells used for the experiments were of passage number 31. Two flasks of cells were prepared in media containing 20% v/v FCS with 10% dimethylsulphoxide and banked down into liquid nitrogen for later use if necessary.

A total of 16 T25 cm$^3$ flasks were used. Each flask was seeded with 8.5×10$^5$ cells/cm$^3$ and 4 cm$^3$ media added. The cells were allowed to adhere to the culture flask overnight. The following morning the flasks were observed under the light microscope and the cells appeared 50-60% confluent. The cells from two of the flasks were harvested (see below) for the t=0 time point.

The remaining 14 flasks were available for testing with casuarine (8). Seven of these (untreated group) had their media changed to 7 cm$^3$ of fresh media containing 10% FCS, penicillin and streptomycin (as before), whilst the remaining seven were incubated with fresh media supplemented with 0.75 mM casuarine (treated group).

Cells were harvested at t=1.5 hours, t=28 hours, t=62 hours and t=86 hours.

Harvesting of Cells and Cell Counting

The cells were harvested using a non-enzymatic method. At each of the time points the cells were viewed under the inverted light microscope and the morphology evaluated. Before harvesting, the cells were washed with sterile PBS, three times, 7 cm$^3$ per wash. The cells were then scraped from the flasks using a sterile cell scraper and transferred to Grenier tubes. The cells were quickly passed through a 21G2 gauge needle to disaggregate the cells. Cells were then pelleted by centrifugation at 1500 g/5 min and resuspended in a known volume of PBS. The number of cells was then counted in a haemocytometer and cell viability evaluated by mixing 0.1 cm$^3$ of each cell suspension with a drop of trypan blue solution. Each of the cell pellets was frozen at −80° C. until glycan release and analysis.

Homogenisation

The cell pellets were placed in an iced water bath and allowed to thaw. The pellets were then homogenized in a total of 4 cm$^3$ (made up to volume with deionized water). An Ultraturrax T25 homogeniser was used for this purpose, with the blade speed set to 22,500 rpm. The samples were maintained on ice and 3 bursts, each of 10 sec, were applied with a period of approximately 1 min between each homogenisation step to allow the froth the settle. The blade was washed carefully between each of the samples to prevent sample cross-contamination. The homogenates were stored in 1 cm$^3$ aliquots at −80° C. prior to the protein assay and glycan release.

Protein Assay

Evaluated using the BioRad protein assay according to the manufacturer's instructions. BSA was used as standard. Each of the homogenate samples was tested in duplicate using 100 μl aliquots from each time point Glycan Release For the time points of 62 hours and 86 hours the equivalent of 25 μg of protein was taken and dried for 3 hours on a centrifugal evaporator (without heating). For the earlier time points, whose protein concentration could not be assessed with the protein assay, 200 μl was taken and dried down ready for glycan release. Release was confirmed using 25 μg of fetuin from foetal calf serum.

Glycans were incubated at 37° C. overnight with N-glycosidase F (Roche Biosciences Cat. No. 1365185, Lot. No. 9280212/31) at a final concentration of 5U enzyme in 25 μl of sample all in 20 mM sodium phosphate buffer pH 7.2. After the incubation step, the samples were loaded onto prewashed and primed Ludger Clean E cartridges (Cat. No. LC-E10-A6). The glycans were eluted according to the manufacturer's instructions and dried by centrifugal evaporation overnight.

Glycan Labeling

The glycans were labeled by reductive amination, for 2 hours at 65° C., according to the method described by Bigge et al. (1995) Anal. Biochem. 230(2): 229-238. The incubation mixture was then "cleaned up" to remove any unconjugated fluorophore by spotting the samples onto Whatman 3MM paper and running in a descending chromatography tank with a mobile phase of 4:1:1 butanol:ethanol:water overnight. Glycans were then eluted with 0.5 cm$^3$ methanol and 2×1 cm$^3$ HPLC grade water then filtered through a 0.2 μm syringe top filter.

Analysis Using Normal Phase HPLC

The glycans were separated on a normal phase (hydrophilic interaction) HPLC column (LudgerSep N1 amide) 4.6×25 cm in size.

The basis of the separation is described in Guile et al. (1996) Anal. Biochem. 240(2): 210-226. The column was fitted to a Dionex BioLC system with autosampler and switching pump heads and in-line mixer. The column was maintained at 30° C. and the glycans detected using a Perkin Elmer LS30 fluorimeter with excitation λ=330 nm and emission λ=420 nm, the gain was set to 2. The buffer system used was the high salt system, with acetonitrile as buffer A and 0.25M ammonium formate pH4.4 as buffer B. Flow rate was maintained at 0.3 cm$^3$/min throughout.

The protocol used is summarized below in Table 8.1, below.

| Time (min) | % A | % B | Comment |
|---|---|---|---|
| 0 | 80 | 20 | Elution of N-linked glycans |
| 132 | 47 | 53 | |
| 135 | 0 | 100 | Elution of large charged glycans |
| 142 | 0 | 100 | |
| 145 | 80 | 20 | Re-equilibration |
| 180 | 80 | 20 | End of run |

An 80 µl aliquot of each of the glycan mixtures was loaded onto the column and the elution position compared, with reference to a hydrolysate of dextran.

Summary of Results and Conclusions

At the initial harvest point and the 28 hour time point, there was no obvious difference between the glycans released from the treated and untreated cells (data not shown). However, at the 62 and 86 hour time points, the untreated cells showed a marked preponderance of larger N-linked glycans than their treated counterparts (data not shown). In addition, the overall signal (amount of fluorescently labeled glycan) was greater in the untreated group.

The results show that casuarine can inhibit glycan synthesis and/or N-linked glycosylation in breast cancer cells.

Example 9

Effect on Glucose Transport

The effect of casuarine (8) and castanospermine (20) on the initial rate of Na$^+$-dependent D-glucose uptake into ovine intestinal brush border membrane vesicles was examined in a competition assay with labeled D-glucose. The results are shown in Table 9.1, below:

| Compound | Reference | Glucose uptake (pmol s$^{-1}$mg$^{-1}$) |
|---|---|---|
| None (control) | | 240 |
| Casuarine | 8 | 265 |
| Castanospermine | 20 | 225 |

It can be seen that glucose transport was slightly inhibited by castanospermine but slightly stimulated by casuarine.

Example 10

Increasing the Th1:Th2 Response Ratio in a Non-Healing Leishmaniasis Model

Leishmaniasis is a classic model of a Th1 disease: non-healing cutaneous lesions arise from an undesirable polarization of the immune response which becomes heavily Th2-skewed.

In order to study the ability of the compounds of the invention to increase the Th1:Th2 response ratio in this disease model (and so promote a healing Th1 response), spleen cells from *Leishmania major* infected BALB/c mice having a non-healing cutaneous infection were stimulated with parasite antigen (Table 10.1) or polyclonally with anti-CD3 (Table 10.2) in the presence of 3,7-diepi-casuarine (10).

TABLE 10.1

Reversal of the inability of T-cells to produce IFN-γ in a non-healing mouse model

| Treatment | IFN-γ (ng/ml) |
|---|---|
| None (control) | ~0.5 |
| L. major Ag | ~0.5 |
| 3,7-diepi-casuarine (10) | ~0.5 |
| 3,7-diepi-casuarine (10) + L. major Ag | 5.5 |

TABLE 10.2

Downregulation of Th2 cytokine response in a non-healing mouse model

| Treatment | IL-5 (pg/ml) |
|---|---|
| None (control) | 50 |
| aCD3 | 240 |
| 3,7-diepi-casuarine (10) + aCD3 | 150 |

It can be seen that the presence of 3,7-diepi-casuarine (10) enhances IFN-γ (associated with a healing Th1 response) whilst suppressing the Th2 response (via downregulation of the Th2 cytokine IL-5). The Th2-skewed immune response profile associated with a non-healing disease was clearly reversed ex vivo by 3,7-diepi-casuarine (10).

Example 11

Synthesis of 3,7-diepi-casuarine (10)

General Experimental

All reactions were carried out under an atmosphere of argon at room temperature using anhydrous solvents unless otherwise stated. Anhydrous solvents were purchased from Fluka Chemicals and were used as supplied. Reagents were supplied from Aldrich, Fluka and Fisher and were used as supplied. Thin layer chromatography (Tlc) was performed on aluminium sheets pre-coated with Merck 60 $F_{254}$ silica gel and were visualised under ultra-violet light and staining using 6% phosphomolybdic acid in ethanol. Silica gel chromatography was carried out using Sorbsil C60 40/60 silica gel under a positive atmosphere. Amberlite IR-120, strongly acidic ion-exchange resin was prepared by soaking the resin in 2M hydrochloric acid for at least two hours followed by elution with distilled water until the eluant reached pH 5. Dowex: 50WX8-100 was prepared by soaking the resin with 2M hydrochloric acid for at least two hours followed by elution with distilled water until neutral. Infrared spectra were recorded on a Perkin-Elmer 1750 IR Fourier Transform spectrophotometer using thin films on sodium chloride plates. Only characteristic peaks are recorded. Optical rotations were measured on a Perkin-Elmer 241 polarimeter with a path length of 1 dm. Concentrations are quoted in g/100 mL. Nuclear magnetic resonance spectra were recorded on a Bruker DQX 400 spectrometer in the stated deuterated solvent. All spectra were recorded at ambient temperature. Chemical shifts (δ) are quoted in ppm and are relative to residual solvent as standard. Proton spectra ($\delta_H$) were recorded at 400 MHz and carbon spectra ($\delta_C$) at 100 MHz.

2,3:5,6:7,8-Tri-O-isopropylidene-D-erythro-L-talo-octono-1,4-lactone (Qc)

5,6:7,8-Di-O-isopropylidene-D-erythro-L-galacto-octono-1,4-lactone (Qb)

Sodium cyanide (7.02 g, 142 mmol) was added to a stirred solution of D-glycero-D-gulo-heptose (Qa, 21 g, 100 mmol)

in water (300 ml). The reaction mixture was stirred at room temperature for 48 h, heated at reflux for 48 h and passed through a column containing Amberlite IR-120 (strongly acidic ion-exchange resin, 300 ml). The eluent was concentrated under reduced pressure and the residue dried in vacuo for 24 hours. The resulting foam was treated with acetone (500 ml) and sulphuric acid (5.4 ml) in the presence of anhydrous copper sulphate (10 g, 62 mmol) at room temperature for 48 h. T.l.c analysis indicated the presence of two major products (ethyl acetate:cyclohexane, 1:1; $R_f$ 0.72, 0.18). The reaction mixture was filtered and the filtrate was treated with sodium bicarbonate (50 g) for 24 h at room temperature. Solid residues were removed by filtration and the filtrate was concentrated under reduced pressure. The resulting crude yellow syrup was purified by silica gel chromatography providing 2,3:5,6:7,8-tri-O-isopropylidene-D-erythro-L-talo-octono-1,4-lactone Qc as a colourless syrup ($R_f$ 0.72; 7.672 g; 21%;) and 5,6:7,8-di-O-isopropylidene-D-erythro-L-galacto-octono-1,4-lactone Qb as a clear oil ($R_f$ 0.18; 8.105 g; 25%) 2,3:5,6:7,8-tri-O-isopropylidene-D-erythro-L-talo-octono-1,4-lactone Qc : $\delta_H$ (CDCl$_3$) 1.29, 1.33, 1.35, 1.38, 1.42, 1.48 (6×s, 18H, 3×C(CH$_3$)$_2$), 3.93-3.99 (m, 2H, H-8$_a$, H-7), 4.03-4.07 (m, 2H, H-5, H-6), 4.15 (dd, 1H, $J_{8a,8b}$ 8.7 $J_{8b,7}$ 6.1, H-8$_b$), 4.75-4.78 (m, 3H, H-2, H-3, H-4); $\delta_C$ (CDCl$_3$) 25.23, 25.51, 26.00, 26.71, 26.73, 27.16 (3×C(CH$_3$)$_2$), 67.93, 74.93, 76.33, 76.69, 78.65, 79.40, 80.06, 109.95, 110.72, 113.19, 174.27; $v_{max}$ (film) 1793. 5,6:7,8-di-O-isopropylidene-D-erythro-L-galacto-octono-1,4-lactone Qb : $\delta_H$ (d$_6$-acetone) 1.28, 1.32, 1.34, 1.35 (4s, 12H, 2×C(CH$_3$)$_2$), 3.92 (1H, m, H-8$_a$), 3.98 (m, 1H, H-7), 4.14 (m, 2H, H-5, H-8$_b$), 4.23-4.25 (m, 2H, H-4, H-6), 4.35-4.40 (m, 2H, H-2, H-3); $\delta_C$ (d$_6$-acetone) 25.31, 25.87, 26.72, 27.31, 68.06, 75.15, 75.23, 77.51, 78.05, 78.41, 79.01, 110.06, 110.31, 174.25; $v_{max}$ (film) 1793, 3541.

2,3:5,6-Di-O-isopropylidene-D-erythro-L-talo-octono-1,4-lactone Qd

A solution of 2,3:5,6:7,8-tri-O-isopropylidene-D-erythro-L-talo-octono-1,4-lactone (Qc, 3.8 g, 10.6 mmol) was treated with acetic acid:water (2:3, 100 ml) at 50° C. for 2 h. T.l.c analysis (ethyl acetate:cyclohexane, 1:1) indicated the disappearance of the starting material ($R_f$ 0.72) and the presence of a more polar compound ($R_f$ 0.15). The solvent was removed under reduced pressure and the residue was purified by silica gel chromatography (ethyl acetate:cyclohexane, 1:1 to 3:1) yielding 2,3:5,6-di-O-isopropylidene-D-erythro-L-talo-octono-1,4-lactone Qd as a clear oil (3.23 g, 94%): $\delta_H$ (CD$_3$OD) 1.28, 1.38, 1.43 (3×s, 12H, 2×C(CH$_3$)$_2$), 3.59 (dd, 1H, $J_{8a,7}$ 5.40 $J_{8a,8b}$ 11.41, H-8$_a$), 3.66-3.69 (m, 1H, H-7), 3.74 (dd, 1H, $J_{8ab,7}$ 2.90 Hz, H-8$_b$), 4.01 (app t, 1H, $J_{6,7}$ 7.62 Hz, H-6), 4.24 (dd, 1H, $J_{5,6}$ 8.17 Hz $J_{5,4}$ 0.89 Hz, H-5), 4.79-4.81 (m, 2H, H-3, H-4), 4.89-4.91 (m, 1H, H-2); $\delta_C$ (CD$_3$OD) 24.62, 25.42, 26.05, 26.49, 63.86, 73.81, 75.40, 75.91, 79.18, 70.90, 80.78, 110.53, 113.09, 175.76; $v_{max}$ (film) 1791, 3478; [α]$_D$ −35.7 (c 1, CHCl$_3$).

8-O-tert-Butyldimethylsilyl-2,3:5,6-di-O-isopropylidene-D-erythro-L-talo-octono-1,4-lactone Qe To a solution of 2,3:5,6-di-O-isopropylidene-D-erythro-L-talo-octono-1,4-lactone (Qd, 3.18 g, 10 mmol) in N,N-dimethylformamide (40 ml) was added tert-butyldimethylsilyl chloride (1.808 g, 12 mmol) and imidazole (1.361 g, 20 mmol). The reaction mixture was stirred at room temperature for 16 h after which t.l.c. analysis (ethyl acetate:cyclohexane, 1:1) showed no starting material ($R_f$ 0.15) and the formation of one major product ($R_f$ 0.63). The solvent was removed under reduced pressure and the residue was partitioned between ethyl acetate and brine. The aqueous layer was extracted with ethyl acetate and the combined organic layers were dried (MgSO$_4$), filtered and the solvent removed. The resulting pale oil was purified by silica gel chromatography (ethyl acetate:cyclohexane, 0:1 to 1:2) to give 8-O-tert-butyldimethylsilyl-2,3:5,6-di-O-isopropylidene-D-erythro-L-talo-octono-1,4-lactone Qe as a clear oil (3.612 g, 85%): $\delta_H$ ((CDCl$_3$) 0.04 (br s, 6H, 2×CH$_3$), 0.86 (s, 9H, C(CH$_3$)$_3$), 1.23, 1.30, 1.32, 1.41 (4×s, 12H, 2×C(CH$_3$)$_2$), 3.63-3.67 (m, 2H, H-8$_a$, H-7), 3.76 (br d, 1H, H-8$_b$), 3.96 (app t, $J_{6,7}$ 8.21 $J_{6,5}$ 7.98, H-6), 4.08 (br d, 1H, H-5), 4.72 (br s, 2H, H-2, H-3), 4.78 (br s, 1H, H-4); $\delta_C$ (CDCl$_3$) −5.52, −5.45, 18.25, 25.51, 25.80, 25.93, 26.68, 27.18, 63.95, 72.97, 74.88, 74.93, 78.71, 79.63, 79.87, 110.34, 113.00, 174.42; $v_{max}$ (film) 1794, 3570; [α]$_D$ −20.1 (c 1, CHCl$_3$).

7-Azido-8-O-tert-butyldimethylsilyl-7-deoxy-2,3:5,6-di-O-isopropylidene-L-threo-L-talo-octono-1,4-lactone Qf A solution of 8-O-tert-butyldimethylsilyl-2,3:5,6-di-o-isopropylidene-D-erythro-L-talo-octono-1,4-lactone (Qe, 3.5 g, 8.2 mmol) in a pyridine:dichloromethane mixture (1:4, 25 ml) was cooled to −30° C. Trifluoromethanesulfonic anhydride (3.5 g, 2.09 ml, 12.4 mmol) was added portion-wise and the mixture was stirred for 2 h. T.l.c analysis (ethyl acetate:cyclohexane, 1:3) indicated the disappearance of starting material ($R_f$ 0.38) and the presence of a less polar product ($R_f$ 0.48). The reaction mixture was concentrated under reduced pressure and the residue was partitioned between ethyl acetate and 0.5 M hydrochloric acid. The organic layer was washed with brine, dried (MgSO$_4$), filtered and concentrated under reduced pressure. The resulting crude pale orange residue was treated with sodium azide (807 mg, 12.4 mmol) in N,N-dimethylformamide (25 ml) for 16 h. T.l.c. analysis (ethyl acetate:cyclohexane, 1:4) indicated the disappearance of the intermediate triflate ($R_f$ 0.42) and the presence of a more polar compound ($R_f$ 0.40). The reaction solvent was removed in vacuo and the residue was partitioned between ethyl acetate and brine. The aqueous layer was extracted with ethyl acetate and the combined organic layers were dried (MgSO$_4$), filtered and concentrated in vacuo. The resulting crude residue was purified by silica gel chromatography (ethyl acetate:cyclohexane, 0:1 to 1:4) providing 7-azido-8-O-tert-butyldimethylsilyl-7-deoxy-2,3:5,6-di-O-isopropylidene-L-threo-L-talo-octono-1,4-lactone Qf as a colourless oil (3.026 g, 81%): $\delta_H$ (CDCl$_3$) 0.11 (2×s, 6H, 2×CH$_3$), 0.91 (s, 9H, C(CH$_3$)$_3$), 1.30, 1.38, 1.41, 1.47 (4×s, 12H, 2× C(CH$_3$)$_2$), 3.41-3.45 (m, 1H, H-7), 3.87 (dd, 1H, $J_{8a,7}$ 5.37 Hz $J_{8a,8b}$ 10.81 Hz, H-8$_a$), 3.92 (dd, 1H, $J_{8b,7}$ 7.32 Hz, H-8$_b$), 4.19-4.24 (m, 2H, H-5, H-6), 4.61 (br s, 1H, H-4), 4.75-4.79 (m, 2H, H-2, H-3); $\delta_C$ (CDCl$_3$) −5.59, −5.56, 18.14, 25.54, 25.73, 26.09, 26.71, 26.98, 61.61, 63.19, 67.94, 74.84, 74.94, 75.47, 78.36, 78.66, 110.90, 113.37, 174.02; $v_{max}$ (film) 1796, 2111; [α]$_D$+36.7 (c 1, CHCl$_3$).

7-Azido-8-O-tert-butyldimethylsilyl-7-deoxy-2,3:5, 6-di-O-isopropylidene-L-threo-L-talo-octitol Qg 7-azido-8-O-tert-butyldimethylsilyl-7-deoxy-2,3:5,6-di-O-isopropylidene-L-threo-L-talo-octono-1,4-lactone (Qf, 3.00 g, 6.6 mmol) was dissolved in tetrahydrofuran (40 ml) and was cooled to 0° C. Lithium borohydride (216 mg, 9.9 mmol) was added and the mixture was stirred at 0° C. to room temperature for 24 h. T.l.c. analysis (ethyl acetate:cyclohexane, 1:1) indicated the disappearance of the starting material ($R_f$ 0.76) and the presence of a more polar compound ($R_f$ 0.45). The reaction was quenched through the addition of ammonium chloride (sat. aq.) and the partitioned between ethyl acetate and brine. The aqueous layer was extracted with ethyl acetate (2×) and the combined organic layers were dried ($MgSO_4$), filtered and the solvent removed. The resulting crude residue was purified by silica gel chromatography (ethyl acetate:cyclohexane, 1:3 to 1:1) affording 7-azido-8-O-tert-butyldimethylsilyl-7-deoxy-2,3:5,6-di-O-isopropylidene-L-threo-L-talo-octitol Qg as a colourless syrup (2.476 g, 82%): $\delta_H$ ($CDCl_3$) 0.10 (s, 6H, 2×$CH_3$), 0.91 (s, 9H, $C(CH_3)_3$), 1.36, 1.41, 1.42, 1.48 (4×s, 12H, 2×$C(CH_3)_2$), 3.43-3.47 (m, 1H, H-7), 3.66 (br d, 1H, H-4), 3.79-3.92 (m, 4H, H-1, H-1$_a$, H-8, H-8$_a$), 4.10-4.14 (m, 2H, H-2, H-3), 4.30-4.38 (m, 2H, H-5, H-6); $\delta_C$ ($CDCl_3$) −5.61, −5.51, 18.14, 25.18, 25.71, 26.87, 27.07, 27.86. 60.65, 62.39, 63.66. 67.62, 75.90. 76.91, 77.18, 77.49, 108.63, 110.16; $v_{max}$ (film) 2109, 3536; $[\alpha]_D$ +46.6 (c 1, $CHCl_3$).

7-Azido-8-O-tert-butyldimethylsilyl-7-deoxy-2,3:5,6-di-O-isopropylidene-1,4-di-O-methanesulphonyl-L-threo-L-talo-octitol Qh 7-Azido-8-O-tert-butyldimethylsilyl-7-deoxy-2,3:5,6-di-O-isopropylidene-L-threo-L-talo-octitol (Qg, 2.4 g, 5.3 mmol) was dissolved in pyridine (20 ml) and was added to a solution of 4-dimethylamino pyridine (64 mg, 0.53 mmol) and methanesulfonyl chloride (4.814 g, 3.253 ml, 42 mmol) in pyridine (20 ml) and stirred for 2 h. T.l.c analysis (ethyl acetate:cyclohexane, 1:2, double elution) revealed the disappearance of starting material ($R_f$ 0.33) and the presence of a more hydrophobic product ($R_f$ 0.43). The solvent was removed under educed pressure and the residue was partitioned between ethyl acetate and brine. The aqueous layer was extracted with ethyl acetate and the combined organic layers were dried ($MgSO_4$), filtered and concentrated under reduced pressure. The resulting crude residue was purified by silica gel chromatography (ethyl acetate:cyclohexane, 1:2) giving 7-azido-8-O-tert-butyldimethylsilyl-7-deoxy-2,3:5,6-di-O-isopropylidene-1,4-di-O-methanesulfonyl-L-threo-L-talo-octitol Qh as a colourless oil (2.973 g, 92%): $\delta_H$ ($CDCl_3$) 0.11, 0.12 (2×s, 6H, 2×$CH_3$), 0.91 (s, 9H, $C(CH_3)_3$), 1.41, 1.44, 1.46, 1.56 (4×s, 12H, 2×$C(CH_3)_2$), 3.08 (s, 3H, $SO_2CH_3$), 3.21 (s, 3H, $SO_2CH_3$), 3.49 (ddd, 1H, $J_{7,6}$ 2.82 Hz, $J_{7,8}$ 5.46 Hz, $J_{7,8a}$ 7.94 Hz, H-7), 3.87-3.97 (m, 2H, H-8, H-8$_a$), 4.19 (dd, 1H, $J_{6,5}$ 2.30 Hz, H-6), 4.24-4.31 (m, 2H, H-1, H-5), 4.36 (dd, 1H, $J_{3,4}$ 2.96 Hz, $J_{3,2}$ 6.62 Hz, H-3), 4.49-4.53 (m, 1H, H-2), 4.69 (dd, 1H. $J_{1a,2}$ 2.39 Hz, $J_{1a,1}$ 10.83 Hz, H-1$_a$), 5.11 (app t, 1H, H-4); $\delta_C$ ($CDCl_3$) −5.56, 18.18, 25.76, 26.24, 26.78, 26.89, 27.56, 37.75, 39.02, 60.90, 63.57, 70.44, 76.00, 76.07, 76.46, 77.18, 77.32, 109.01, 110.68; $v_{max}$ (film) 2113; $[\alpha]_D$ −16.2 (c 1, $CHCl_3$).

7-Azido-7-deoxy-1,4-di-O-methanesulphonyl-L-threo-L-talo-octitol Qi

7-Azido-8-O-tert-butyldimethylsilyl-7-deoxy-2,3:5,6-di-O-isopropylidene-1,4-di-O-methanesulfonyl-L-threo-L-talo-octitol (Qh, 2.90 g, 4.7 mmol) was treated with a trifluoracetic acid:water mixture (1:1, 40 ml) for 3 h. T.l.c. analysis (ethyl acetate) showed the disappearance of starting material ($R_f$ 0.9) and the presence of a more polar product ($R_f$ 0.12). The solvent was removed under reduced pressure and the residue was co-evaporated with toluene and dried under vacuum. Purification by silica gel chromatography (ethyl acetate:cyclohexane, 1:1 to 1:0) yielded 7-azido-7-deoxy-1, 4-di-O-methanesulphonyl-L-threo-L-talo-octitol Qi as a colourless oil (1.677 g, 85%): $\delta_H$ ($CD_3OD$) 3.12 (s, 3H, $SO_2CH_3$), 3.21 (s, 3H, $SO_2CH_3$), 3.61-3.71 (m, 2H, H-7, H-8), 3.78-3.82 (m, 2H, H-6, H-8$_a$), 3.98-4.05 (m, 2H, H-2, H-3), 4.11-4.13 (m, 1H, H-5), 4.34 (dd, 1H, $J_{1,2}$ 4.87 Hz, $J_{1,1a}$ 10.44 Hz, H-1), 4.45 (dd, 1H, $J_{1,2}$ 1.87 Hz, H-1$_a$), 5.00 (dd, 1H, $J_{4,3}$ 1.91 Hz, $J_{4,5}$ 6.15 Hz, H-4); $\delta_C$ ($CD_3OD$) 36.17, 38.11, 61.84, 66.62, 69.09, 70.33, 70.45, 71.08, 72.55, 86.41; $v_{max}$ (film) 2113; $[\alpha]_D$ −9.1 (c 1, $H_2O$).

(1R,2R,3S,6S,7R,7aR)-3-(Hydroxymethyl)-1,2,6,7-tetrahydroxypyrrolizidine Qj

[3,7-diepi-Casuarine]

7-Azido-7-deoxy-1,4-di-O-methanesulphonyl-L-threo-L-talo-octitol (Qi, 1.6 g, 3.78 mmol) was dissolved in water (30 ml) and was treated with 10% palladium on carbon (400 mg) under an atmosphere of hydrogen for 16 h. T.l.c analysis (ethyl acetate:methanol, 9:1) indicated the disappearance of starting material ($R_f$ 0.75) and the presence of a more polar product ($R_f$ 0.05). Palladium was removed by filtration and the filtrate was treated with sodium acetate (930 mg, 11.34 mmol) at 60° C. for 16 h. The reaction mixture was cooled and the solvent removed in vacuo. The crude brown oil was purified by ion-exchange chromatography (Dowex 50WX8-100, eluting with 2M ammonium hydroxide) to afford (1R,2R,3S, 6S,7R,7aR)-3-(hydroxymethyl)-1,2,6,7-tetrahydroxypyrrolizidine [3,7-diepi-Casuarine] Qj as a brown glass (671 mg, 87%): $\delta_H$ ($D_2O$) 2.81-2.92 (m, 2H, H-5, H-5$_a$), 3.16 (dd, 1H, $J_{3,2}$ 5.91 Hz, $J_{3,8}$ 10.74 Hz, H-3), 3.30 (app t, 1H, J 3.78 Hz, H-7$_a$), 3.76 (dd, 1H, $J_{8,8a}$ 6.35 Hz, H-8), 3.87 (dd, 1H, H-8$_a$), 4.01 (d, 1H, $J_{2,1}$ 3.55 Hz, H-2), 4.04-4.12 (m, 2H, H-6, H-7), 4.29 (app t, 1H, H-1); $\delta_C$ ($D_2O$) 49.32, 57.29, 63.78, 70.41, 72.59, 72.65, 74.47, 78.25; $[\alpha]_D$ −21.1 (c 0.5, $H_2O$).

Equivalents

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:
1. A method of treatment of a disease or condition comprising administering to a patient in need of such treatment a therapeutically effective amount of a polyhydroxylated pyrrolizidine compound selected from the formulae below:

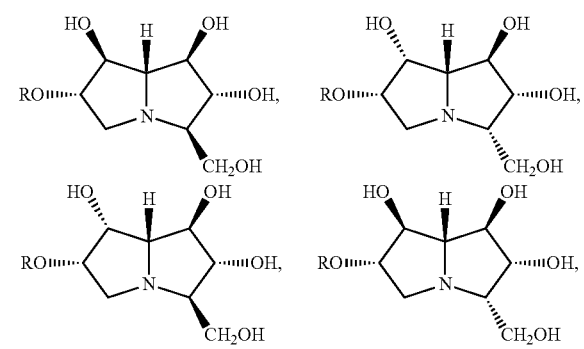

-continued

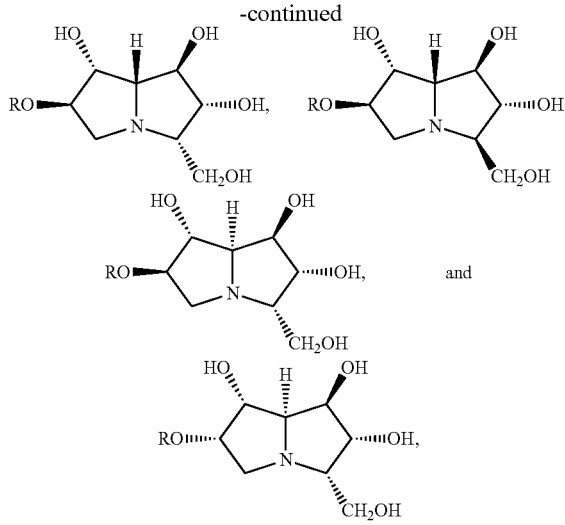

or a pharmaceutically acceptable salt or $(C_1-C_4)$acyl derivative thereof, wherein R is selected from the group consisting of hydrogen, straight or branched, unsubstituted or substituted, saturated or unsaturated acyl, alkyl, alkenyl, alkynyl and aryl groups, and a saccharide moiety; and wherein said disease or condition is selected from a bacterial infection, a herpes virus infection, an Ebola virus infection, lung cancer, breast cancer and melanoma.

2. A method according to claim 1 wherein the pyrrolizidine compound, salt or derivative has the formula:

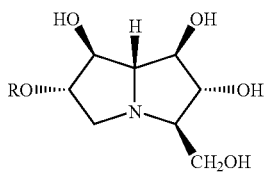

wherein R is selected from the group consisting of hydrogen, straight or branched, unsubstituted or substituted, saturated or unsaturated acyl, alkyl, alkenyl, alkynyl and aryl groups.

3. A method according to claim 1 wherein the pyrrolizidine compound is an acyl derivative.

4. A method according to claim 3 wherein the pyrrolizidine acyl derivative is acylated at C-6.

5. A method according to claim 3 wherein the acyl derivative is an alkanoyl derivative selected from acetyl, propanoyl and butanoyl.

6. A method according to claim 1 wherein R is a saccharide moiety.

7. A method according to claim 6 wherein the saccharide moiety is a glucoside or arabinoside moiety.

8. A method according to claim 1 wherein the pyrrolizidine compound is chosen from:

(a) 1R,2R,3R,6S,7S,7aR)-3-(hydroxymethyl)-1,2,6,7-tetrahydroxypyrrolizidine (casuarine), wherein R is hydroaen and having the formula:

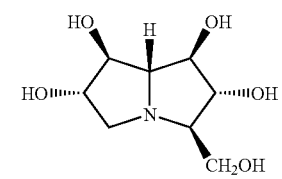

(b) a casuarine glycoside;
(c) casuarine-6-α-D-glucoside of the formula:

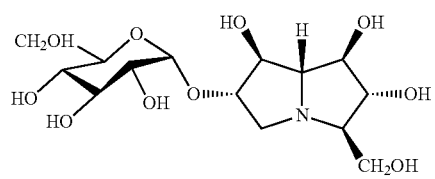

(d) 6-O-butanoylcasuarine;
(e) 3,7-diepi-casuarine;
(f) 7-epi-casuarine;
(g) 3,6,7-triepi-casuarine;
(h) 6,7-diepi-casuarine;
(i) 3-epi-casuarine;
(j) 3,7-diepi-casuarine-6-α-D-gluco side;
(k) 7-epi-casuarine-6-α-D-glucoside;
(l) 3,6,7-triepi-casuarine-6-α-D-glucoside;
(m) 6,7-diepi-casuarine-6-α-D-glucoside;
(n) 3-epi-casuarine-6-α-D-glucoside, or
a pharmaceutically acceptable salt or acyl derivative of any of (a)-(n).

9. A method according to claim 1 wherein said viral infection is selected from Ebola virus herpes simplex virus type 1, herpes simplex virus type 2, herpes genitalis, herpes keratitis, herpes encephalitis, and herpes (varicella) zoster.

10. A method according to claim 1 wherein said bacterial infection is caused by bacteria selected from *Bacillus, Escherichia* and *Francisella*.

11. A method according to claim 1 wherein said polyhydroxylated pyrrolizidine compound is derived from one or more plant species sources selected from:
(a) a member of the taxon Myrtaceae; and
(b) a member of the taxon Casuarinaceae.

12. A method of treatment of a disease or condition comprising administering to a patient in need of such treatment a therapeutically effective amount of a polyhydroxylated pyrrolizidine compound of formula:

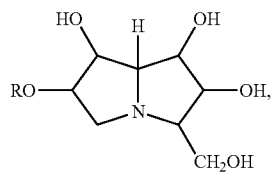

or a pharmaceutically acceptable salt or $(C_1-C_4)$acyl derivative thereof, wherein R is selected from the group consisting of straight or branched, unsubstituted or substituted, saturated or unsaturated acyl, alkyl, alkenyl, alkynyl and aryl groups, and a saccharide moiety; and wherein said disease or condition is selected from a bacterial infection, a herpes virus infection, an Ebola virus infection, lung cancer, breast cancer and melanoma.

13. A method according to claim 12 wherein said polyhydroxylated pyrrolizidine compound is administered as a pharmaceutical composition additionally comprising a pharmaceutically acceptable excipient.

14. A method according to claim 1 wherein said polyhydroxylated pyrrolizidine compound is administered as a pharmaceutical composition additionally comprising a pharmaceutically acceptable excipient.

* * * * *

UNITED STATES PATENT AND TRADEMARK OFFICE
CERTIFICATE OF CORRECTION

| | | |
|---|---|---|
| PATENT NO. | : 8,383,665 B2 | Page 1 of 1 |
| APPLICATION NO. | : 10/543014 | |
| DATED | : February 26, 2013 | |
| INVENTOR(S) | : Watson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 639 days.

Signed and Sealed this
Thirtieth Day of December, 2014

Michelle K. Lee
*Deputy Director of the United States Patent and Trademark Office*